(12) United States Patent
Petrich et al.

(10) Patent No.: US 9,611,504 B2
(45) Date of Patent: Apr. 4, 2017

(54) METHODS OF MEASURING ANALYTES THAT INCLUDE A TEST ELEMENT QUALITY MEASUREMENT BASED UPON INTRINSIC LUMINESCENCE OF A TEST CHEMICAL OF THE TEST ELEMENT

(71) Applicant: Roche Diabetes Care, Inc., Indianapolis, IN (US)

(72) Inventors: Wolfgang Petrich, Bad Schoenborn (DE); Carina Horn, Biblis (DE); Nelli Steinke, Lampertheim (DE); Christian Ringemann, Mannheim (DE); Alexa Freifrau von Ketteler, Ulm (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/277,077

(22) Filed: May 14, 2014

(65) Prior Publication Data
US 2014/0242622 A1    Aug. 28, 2014

Related U.S. Application Data

(63) Continuation of application No. PCT/EP2012/072366, filed on Nov. 12, 2012.

(30) Foreign Application Priority Data

Nov. 14, 2011    (EP) .................................... 11189010

(51) Int. Cl.
| | |
|---|---|
| G01N 33/573 | (2006.01) |
| C12Q 1/52 | (2006.01) |
| A61B 5/145 | (2006.01) |
| G01N 35/00 | (2006.01) |
| A61B 5/1495 | (2006.01) |
| G01N 21/84 | (2006.01) |
| C12Q 1/00 | (2006.01) |
| C12Q 1/32 | (2006.01) |
| G01N 21/64 | (2006.01) |

(52) U.S. Cl.
CPC .............. *C12Q 1/52* (2013.01); *A61B 5/1495* (2013.01); *A61B 5/14532* (2013.01); *C12Q 1/006* (2013.01); *C12Q 1/32* (2013.01); *G01N 21/8483* (2013.01); *G01N 35/00663* (2013.01); *A61B 2560/0233* (2013.01); *G01N 21/6428* (2013.01); *G01N 2035/00673* (2013.01)

(58) Field of Classification Search
None
See application file for complete search history.

(56) References Cited

U.S. PATENT DOCUMENTS

| | | | |
|---|---|---|---|
| 5,527,706 A * | 6/1996 | Kroneis et al. ................. 436/55 |
| 2002/0127623 A1* | 9/2002 | Minshull et al. ............ 435/7.92 |
| 2008/0014655 A1* | 1/2008 | Horn ............................. 436/172 |
| 2009/0146078 A1* | 6/2009 | Colvin et al. ............... 250/459.1 |
| 2009/0208989 A1 | 8/2009 | Petrich et al. |
| 2010/0227348 A1* | 9/2010 | Petrich et al. ................... 435/14 |
| 2012/0053429 A1* | 3/2012 | Trepagnier et al. .......... 600/310 |
| 2012/0250024 A1* | 10/2012 | Noda et al. ................... 356/450 |
| 2013/0052674 A1* | 2/2013 | Horn et al. ...................... 435/14 |

FOREIGN PATENT DOCUMENTS

| | | |
|---|---|---|
| DE | 102008056583 A1 | 5/2010 |
| EP | 0355849 A2 | 2/1990 |
| JP | 201324797 A | 4/2013 |
| WO | 01/60248 A1 | 8/2001 |
| WO | 03/023356 A3 | 3/2003 |
| WO | 2005/106435 A1 | 11/2005 |

OTHER PUBLICATIONS

Bhaumik, Sukesh R. and Sonawat, Haripalsingh M., "Glucose Dehydrogenase from Halobacterium salinarum: Fluorescence Quenching and Binding to NADPH," Physiological Chemistry and Physics and Medical NMR, 1999, pp. 85-92, vol. 31.
Bonneau, Pierre B. et al., "Evidence of a Conformational Change in the Human Cytomegalovirus Protease upon Binding of Peptidyl-Activated Carbonyl Inhibitors," Biochemistry, 1997, pp. 12644-12652, vol. 36.
D'Auria, Sabato et al., "Glucose-sensing proteins from mesophilic and thermophilic bacteria as new tools in diabetes monitoring," Proceedings of SPIE, 2001, pp. 21-31, vol. 4252.
Hilt, Wolfgang et al., "Glucose dehydrogenase from Bacillus subtilis expressed in *Escherichia coli* I: purification, characterization and comparison with glucose dehydrogenase from Bacillus megaterium," Biochimica et Biophysica Acta, 1991, pp. 298-304, vol. 1076.
Iweibo, Idowu, "Protein Fluorescence and Electronic Energy Transfer in the Determination of Molecular Dimensions and Rotational Relaxation Times of Native and Coenzyme-Bound Horse Liver Alcohol Dehydrogenase," Biochimica et Biophysica Acta, 1976, pp. 192-205 , vol. 446.
Matsushita, Kazunobu et al., "Soluble and Membrane-bound Quinoprotein D-Glucose Dehydrogenases of the Acinetobacter calcoaceticus: The Binding Process of PQQ to the Apoenzymes," Bioscience, Biotechnology, and Biochemistry, 1995, pp. 1548-1555, vol. 59, No. 8.
Mendoza-Hernández, Guillermo et al., "Aggregation, dissociation and unfolding of glucose hydrogenase during urea denaturation," Biochimica et Biophysica Acta, 2000, pp. 221-231, vol. 1478.
Moore, Christine M. et al., "Improving the Environment for Immobilized Dehydrogenase Enzymes by Modifying Nafion with Tetraalkylammonium Bromides," Biomacromolecules, 2004, pp. 1241-1247, vol. 5.

(Continued)

*Primary Examiner* — Ralph Gitomer

(57) ABSTRACT

An analytical apparatus is disclosed for detecting at least one analyte in a sample, where in an analyte measurement at least an electrical or optical property changeable by presence of the analyte at least one test chemical of a test element is recorded, and where the analytical apparatus also can perform at least one quality measurement on the at least one test chemical such as an intrinsic luminescence, which is recorded and from the intrinsic luminescence a conclusion is drawn on a quality of the test chemical and thus the test element. Methods also are disclosed for detecting at least one analyte in a sample that include a quality measurement of the at least one test chemical of the test strip.

10 Claims, 7 Drawing Sheets

(56) References Cited

OTHER PUBLICATIONS

Pauly, Hans E. and Pfleiderer, Gerhard, "Conformational and Functional Aspects of the Reversible Dissociation and Denaturation of Glucose Dehydrogenase," Biochemistry, 1977, pp. 4599-4604, vol. 16, No. 21.

Pickup, John C. et al., "Fluorescence-based glucose sensors," Biosensors and Bioelectronics, 2005, pp. 2555-2565, vol. 20.

Scognamiglio, Viviana et al., "Protein-Based Biosensors for Diabetic Patients," Journal of Fluorescence, Sep. 2004, pp. 491-498, vol. 14, No. 5.

Van Duffelen, Marilyn et al., "Nucleotide Dependent Intrinsic Fluorescence Changes of W29 and W36 in Smooth Muscle Myosin," Biophysical Journal, Sep. 2004, pp. 1767-1775, vol. 87.

Yamazaki, Tomohiko et al., "Subunit Analyses of a Novel Thermostable Glucose Dehydrogenase Showing Different Temperature Properties According to Its Quaternary Structure," Applied Biochemistry and Biotechnology, pp. 325-335, vol. 77-79.

\* cited by examiner

METHODS OF MEASURING ANALYTES THAT INCLUDE A TEST ELEMENT QUALITY MEASUREMENT BASED UPON INTRINSIC LUMINESCENCE OF A TEST CHEMICAL OF THE TEST ELEMENT

CROSS-REFERENCE TO RELATED APPLICATIONS

This patent application is a continuation of Int'l Patent Application No. PCT/EP2012/072386; filed 12 Nov. 2012, which claims priority to and the benefit of EP Patent Application No. 11189010.9; filed 14 Nov. 2011. Each patent application is incorporated herein by reference as if set forth in its entirety.

TECHNICAL FIELD

This disclosure relates generally to chemistry and medicine, and more particularly, it relates to methods of detecting test elements having compromised or degraded test chemicals, as well as to analytical apparatuses incorporating the same.

BACKGROUND

Methods of detecting one or more analytes in a sample are generally known in the art. Typically, test elements are employed in interaction with analytical apparatuses that evaluate the test elements. Test elements generally have at least one test chemical, which can be at least one detection reagent for qualitatively and/or quantitatively detecting the analyte.

A great technical challenge with known test elements is stability of the test chemicals. For example, oxygen and moisture can impair quality of test chemicals or of parts thereof. In the art, considerable efforts are known to stabilize test chemicals against such influences and to lower requirements for storage of the test elements and to increase long-term stability. For example, Int'l Patent Application Publication No. WO 2007/012494 describes a test chemical containing stable NAD/NADH derivatives.

Likewise, EP Patent Application Publication No. 2093284 describes stabilizing dehydrogenases with stable coenzymes.

Moreover, EP Patent Application Publication No. 1189064 describes a method of controlling suitability of use of test elements. In the reference, a deviation of a ratio of a control value and a first standard reference value from a first reference ratio is checked, which is formed from a control reference value and a first standard reference value. A checked test element is rejected if the deviation lies outside a pre-specified tolerance range. It is proposed therein the usability of a test element with the aid of a so-called dry blank value measurement of a test field (i.e., an optical measurement of a test field still not wetted with sample fluid). To carry out the control method, it is further proposed that the test element, in addition to having a test field serving for the control of its suitability for use and for carrying out the analysis, contains an integrated reference control means. This method, however, has numerous challenges in practice. For example, the dry blank value measurement, in which a reflectance of the test field is measured before wetting with the sample, provides only a rough check of aging of the test element. In this manner, and within very rough limits, degraded test elements can be excluded with the aid of a discoloration of the test field, which is attributed to a discoloration of a dye contained in the test field. Furthermore, the integrated reference control means places technical demands on the design of the test elements, which are not simply and inexpensively realizable in all cases.

EP Patent Application Publication No. 2221608 describes a method of investigating a body fluid by means of a test tape. To increase measuring reliability, it is proposed therein that a control value is determined from a time- and/or wavelength-dependent change of measurement signals over a duration of a measuring time interval. With the aid of the control value, measurement signals are processed as valid or are discarded as erroneous after measurement. It also is proposed that a test field control value can be determined from a blank value measurement of still unused test fields and the usability of the test field by comparison with a batch control value to discern an influence of the storage time on the test material. It further is proposed to store the batch control value on a storage means assigned to the test tape. This method, however, has numerous challenges in practice. For example, the batch control value is attached to the test elements. In addition, rough degradations of a test chemical also are discernible by a reflectance measurement of a dry blank value, which can be attributed to degradation of a dye and a color change of the test fields connected therewith. Degradations, which are not discernible in this way and which, for example, do not lead to a color change of the test fields, can only be identified and excluded with comparative difficulty.

Int'l Patent Application Publication No. WO 2001/060248 describes methods and devices for non-invasively measuring analyte concentrations, such as glucose, in tissue. In the proposed methods, a target within the tissue of a patient is optically stimulated, the fluorescence of which correlates with the glucose concentration. It is proposed therein to use pepsin digestible collagen cross links (PD-CCL) as a target. Glucose itself has a low intrinsic fluorescence, whereas fluorescence of PDCCL changes depending on the glucose concentration in the tissue of the patient. It also discloses that fluorescence of the target can be dependent on certain effects such as, for example, age, UV exposure, skin color or other effects. Accordingly, it is proposed to use fluorescence signals of the skin with irradiation in the ultraviolet spectral range (UVA) to assess and to take into consideration the state of the collagen matrix.

DE Patent Application Publication No. 10 2008 056583 describes a method and a device for determining reagent quality. In the proposed methods, a carrier element is passed through treatment stations with a test material simultaneously with certain objects. The changes of the test material are recorded and compared with reference data. It is proposed therein to record characteristic properties of the test material caused by the treatment by means of fluorescence.

Int'l Patent Application Publication No. WO 2003/023356 describes methods and devices for non-invasively measuring analyte concentrations in vivo. In the proposed devices, an optical coupler is used to connect a skin surface with a device having a multiplicity of zones. These zones include areas for a multiplicity of purposes, including a calibration of the device, a reading of the skin surface, and a protective function for the device.

The use of fluorophores for detecting glucose concentrations in test strips also is generally known in the art. See, e.g., EP Patent Application Publication No. 1780288 and Int'l Patent Application Publication No. WO 2009/015870. Specifically, glucose-induced changes in fluorescence of proteins and other fluorophores can be used for detecting glucose. See, Pickup et al. (2005) *Biosens. Bioelectron.* 20:2555-2565.

Likewise, the lifetime of alcohol dehydrogenase can be measured by measuring NADH formed in a detection reaction. See, Moore et al. (2004) *Biomacromolecules* 5:1241-1247.

Moreover, urea is known to change of intrinsic fluorescence properties of proteins with their conformation. See, Scognamiglio et al. (2004) *J. Fluoresc.* 14:491-498; and Mendoza-Hernandez et al. (2000) *Biochim. Biophys. Acta* 1478:221-231. Tryptophan also is known to change intrinsic fluorescence of proteins. See, van Duffelen et al. (2004) *Biophys. J.* 87:1767-1775; Bhaumik & Sonawat (1999) *Physiol. Chem. Phys. Med. NMR* 31:85-82; and Mendoza-Hernandez et al. (2000). Similarly, a change of a fluorescence emission of GlucDH-S is known. See, Hilt et al. (1991) *Biochim. Biophys. Acta* 1076:298-304. It is further known that degeneration of GlucDH with urea is reversible. See, Mendoza-Hernandez et al. (2000); and Pauly & Pfleiderer (1977) *Biochem.* 16:4599-4604. Absorption measurements on GlucDH also are described in Yamazaki et al. (1999) *App. Biochem. Biotech.* 325:77-79, wherein an absorption peak was observed at 409 nm. Temperature stress of GlucDH led to the disappearance of this absorption peak. Furthermore, fluorescence was observed, which decreased on a temperature treatment and which was attributed to an unknown cofactor. It was later discovered that the intrinsic fluorescence was caused by FAD. See, Inose et al. (2003) *Biochim. Biophys. Acta* 1645:133-138.

Despite the advances achieved using known detection methods, apparatuses and test chemicals, there still is a residual uncertainty with respect to an aging phenomena of the test elements. This disadvantage presently is address via test elements that are marketed as individual test strips or as test elements with several test chemical areas having an expiry date. By means of a corresponding coding, analytical apparatuses can also recognize whether this expiry date has been exceeded and correspondingly prevent use of aged test elements of this type. Nevertheless, there is the risk, even before expiry of the nominal lifespan, that defective or aged test elements can be used for a measurement. To further address the disadvantage, test elements are supplied in containers in which a drying agent is contained to maintain a low-moisture atmosphere for storage. In some instances, a user is prompted to close this container immediately after removal of a test strip. However, with users having dementia or even children, it cannot always be guaranteed that such a correct treatment of the test elements actually takes place, so that a measurement using degraded test elements cannot be excluded in all details.

For the foregoing reasons, there is a need for additional apparatuses and methods for detecting degraded test elements.

BRIEF SUMMARY

In view of the disadvantages noted above, this disclosure describes analytical apparatuses and methods of measuring an analyte of interest that incorporate a quality measurement on a test element. An inventive concept of the quality measurement includes that an intrinsic luminescence of a test chemical in many cases increases with an aging of test elements. This surprising property being caused by degradation of the test chemical that is associated with a change in an intrinsic luminescence and that can be measured before wetting the test element with a body fluid sample (or other fluidic sample having an analyte of interest). As such, the analytical apparatuses and methods disclosed herein attenuate, avoid or even correct for using degraded test elements, whether it be a degradation from exceeding a storage lifetime or a degradation from an erroneous treatment or storage of test elements. The inventive concept therefore provides certain advantages, effects, features and objects when compared to known apparatuses and methods of measuring an analyte concentration.

In one aspect, analytical apparatuses are provided for detecting at least one analyte in a body fluid sample, where before, during or after an analyte measurement, the apparatuses detect at least one property of at least one test chemical of a test element changeable by presence of the analyte. In some instances, the at least one property is an electrical and/or an optical property.

The analytical apparatuses therefore include at least one analyte measurement device for measuring the analyte and at least one quality measurement device for measuring test element quality. In some instances, the analyte measurement device can be at least one optical measurement device or at least one electrical measurement device. In other instances, the analyte measurement device is an optical measurement device such as an optical analyte detector.

To solve the disadvantage described above, the analytical apparatuses disclosed herein therefore are configured to perform at least one quality measurement on the test chemical of the test element. In some instances, the quality measurement device can be at least one quality detector, such as an optical quality detector, that records at least one recordable property of the test chemical, from which the quality of the test chemical can be concluded. The at least one recordable property can be different from a variable property recorded during the analyte measurement. Thus, during an analyte measurement and/or quality measurement, electrical and/or optical properties of the test chemical can be recorded, which likely will differ. Even if, in both cases, optical properties are recorded, they can be different optical properties such as, for example, a reflectance measurement and/or a color change measurement in the analyte measurement and a fluorescence measurement in the in the quality measurement. In some instances, fluorescence measurements can be carried out in different spectral ranges. In the quality measurement, at least an intrinsic luminescence of the test chemical is recorded, and a quality of the test chemical, such as degradation, is concluded from the intrinsic luminescence.

By the quality measurement, the disadvantages noted above can be avoided in different ways. For one, the quality measurement can be used to assess and/or to correct at least one analyte measurement result. That is, the result of the analyte measurement can be calibrated by means of the quality measurement. For example, at least one item of calibration information can be stored in the analytical apparatus, which, taking into consideration the analyte measurement result and taking into consideration the quality measurement result, generates a measurement result that qualifies or quantifies the analyte in the sample. Alternatively or additionally, the analytical apparatuses can be configured to make possible or to prevent the analyte measurement, or to make possible or to prevent an output of the analyte measurement result to a user or another apparatus after taking the quality measurement result into account. Thus, for example, at least a quality threshold can be specified in the analytical apparatus, with which the quality determined in the quality measurement can be compared. In this manner, a result "Quality OK" or "Quality not OK" can be generated. A subsequent analyte measurement using the test chemical can be enabled or prevented, or, if the analyte measurement has already been carried out, an assessment of the result can take place and not even being communicated to a user or to another apparatus or by the result being communicated with an appropriate message such as, for example, a warning message.

In addition, the analytical apparatuses can be configured so that prior to the quality measurement, one or more items of comparison information are generated, which can take place within the analytical apparatuses or also externally. These items of comparison information can be stored, for example, in the analytical apparatus. Generally, in the quality measurement, at least one quality measurement value can be generated and can be compared with the one or more items of comparison information such as one or more threshold values. In this manner, the at least one item of information of the quality can be generated from at least one comparison. This information can be of several gradations so that the quality of the test chemical can be classified into one or more continuous or discontinuous categories.

In some instances, the analytical apparatuses can be configured to perform the quality measurement at least once before the analyte measurement. Thus, for example, the analyte measurement can be preceded in time by at least one quality measurement. As explained above, the analyte measurement reporting can be influenced by the result of the quality measurement so that the analyte measurement result is not reported to the user or is influenced in another way according to the result of the at least one quality measurement.

To facilitate the analyte measurement and/or quality measurement, the analytical apparatuses can include corresponding devices and/or elements. For example, the analytical apparatuses can include at least one analyte detector such as an optical analyte detector and at least one light source.

The analytical apparatuses can use a recorded intrinsic luminescence or a value correlating with the intrinsic luminescence such as, for example, a detector signal directly as the quality of the test chemical. Alternatively or additionally, the quality can be calculated or determined in another way using the recorded intrinsic luminescence. Thus, from the intrinsic luminescence firstly, an activity of at least one enzyme of the test chemical and/or at least one coenzyme of the test chemical can be concluded and/or an activity of another substance of the test chemical.

The analytical apparatus can be configured to draw conclusions as to a degradation of the test element if the intrinsic luminescence exceeds at least one predetermined threshold. It was found that an intrinsic luminescence of the test chemical in many cases increases with an aging of test elements and in particular of the test chemical. With test chemicals that include at least one enzyme such as, for example, glucose oxidase and/or glucose dehydrogenase, conclusions can be drawn from an increase in the intrinsic fluorescence of the test chemical on an aging of the test chemical. In view of these empirical observations, it can remain undecided whether this increase in the intrinsic fluorescence is caused, for example, by an intrinsic fluorescence of degradation products formed in the degradation and/or whether other processes play a role such as, for example, a conformation change of the test chemical during the aging process and thereby a reduced fluorescence quenching.

To detect increases in intrinsic luminescence, one or more threshold values can be specified as the threshold. For example, the luminescence can be compared directly with the at least one threshold value, or other characteristic values can also firstly be determined from the at least an intrinsic luminescence, which then are compared with the at least one threshold value.

The quality of the test chemical determined in the quality measurement can be used in various ways. For example, if it is established that the quality does not fulfill one or more specified conditions (i.e., the intrinsic luminescence exceeds one or more threshold values), a preceding analyte measurement can be discarded, a subsequent analyte measurement can be prevented, or a warning can be issued to the user. Alternatively or additionally, the quality determined can be taken into consideration in evaluating the analyte measurement during calculation of the analyte concentration in the sample from the variable property of the test chemical determined in the analyte measurement taking into consideration the quality determined in the quality measurement. Thus, the analytical apparatus can be configured to calculate a concentration of the analyte in the sample such as, for example, indicated in a mass of the analyte per volume of the sample or in a mass of the analyte per mass of the sample, taking into consideration the quality of the test chemical. This can take place in that a correction of the analyte measurement or of the concentration of the analyte calculated from the analyte measurement takes place, which is dependent on the quality determined. Thus, simple correction factors can be used for linear corrections. Non-linear corrections, however, also are possible. For example, one or more correction functions can be used that can be stored in a data store of the analytical apparatus, which carry out the calculation of the analyte concentration according to the quality determined. These correction functions can be linear or non-linear.

In some instances, the correction functions can be determined empirically. For example, in the quality measurement, an enzyme activity can be determined, and lower conversion of the analyte resulting from a decrease in an enzyme activity of the test chemical during an enzymatic detection can be taken into consideration when evaluating analyte measurement.

For carrying out the at least one quality measurement, the analytical apparatuses therefore include at least one optical quality detector, which can be integrated completely or partially into the analyte detector or can be constructed completely or partially separated from the at least one optional analyte detector. In some instances, the optical quality detector is completely or partially separate from the analyte detector and includes at least one light source and/or at least one detector. Thus, the analyte detector and the optical quality detector can have different light sources and/or different photodetectors. Alternatively or additionally, at least one light source and/or at least one photodetector can be employed both in the analyte detector and the optical quality detector.

In some instances, light from the light source for the optical analyte detector can be spectrally different from the light made available for the optical quality detector. In other instances, the light is spectrally identical. For example, the optical analyte detector can have at least one analyte light source producing an analysis light at a wavelength of about 360 nm. The same light source can, simultaneously or with a time lag, also produce an excitation light or other lights for a quality measurement.

Thus, the at least one optical quality detector includes at least one light source to irradiate the test chemical completely or partially with at least one excitation light. In some instances, the light is in an ultraviolet and/or a visible spectral range. For example, at least one excitation light source can be provided at a wavelength range from about 340 nm to about 380 nm, or at about 360 nm. Furthermore, the optical quality detector can include at least one photosensitive element, which can record at least one luminescence of the test chemical qualitatively or quantitatively. For this purpose, at least one photodiode, at least one charge-coupled device (CCD) camera, at least one photodetector or at least one other type of a photosensitive element can be provided. Furthermore, the optical quality detector can include additional optical elements, such as, for example, one or more filters for filtering the excitation light and/or for filtering the luminescence.

In some instances, the analytical apparatus records the intrinsic luminescence in at least two different wavelength regions. For example, a first intrinsic luminescence can be recorded in a first wavelength interval and at least a second intrinsic luminescence in at least a second wavelength interval. The at least one first intrinsic luminescence and the at least one second intrinsic luminescence can be provided or can be recorded integrally by means of the relevant wavelength intervals. Alternatively, a spectral resolution of the recording of the intrinsic luminescences can take place. For example, the optical quality detector can record at least a first intrinsic luminescence or at least a first intrinsic luminescence spectrum in a first wavelength interval and at least a second intrinsic luminescence or at least a second intrinsic luminescence spectrum in at least a second wavelength interval.

For the recording the at least two intrinsic luminescences, different photosensitive elements such as different photodetectors and/or different photodiodes can be provided. Alternatively, the different luminescences can be recorded using one and the same detector by firstly recording luminescence filtered by a first optical filter and subsequently recording luminescence filtered by a second optical filter after a time delay. When using filters of different spectral properties, photosensitive elements having different spectral properties can be employed. Generally, the optical quality detector includes at least one first luminescence detector for recording the first intrinsic luminescence, as well as optionally at least one first optical filter, and at least one second luminescence detector, optionally having at least a second optical filter, for recording the second intrinsic luminescence.

The at least two intrinsic luminescences can be used in various ways to determine quality. In this manner, the analytical apparatus can calculate from the intrinsic luminescence in the at least two different wavelength regions, for example, from the first intrinsic luminescence and the second intrinsic luminescence, at least a quality index characterizing the quality. This quality index can be calculated by a simple quotient formation from the first intrinsic luminescence and the second intrinsic luminescence. Alternatively or additionally, a linear combination of the intrinsic luminescences can be formed. Other functions for calculating the quality index from the at least two intrinsic luminescences also can be used.

It has been shown that a separation of the intrinsic luminescences into intrinsic luminescences in the ultraviolet spectral range and in the visible spectral range can be favorable. Thus, the first intrinsic luminescence can be recorded integrally in a first wavelength range from about 380 nm to about 420 nm, and the second intrinsic luminescence integrally in a second wavelength range of at least about 420 nm or more such as, for example, in a range from about 420 nm to about 650 nm.

As noted above, the optical quality detector can include at least one excitation light source. This at least one excitation light source can be a semiconductor light source. Other light sources, however, also contemplated such as, for example, incandescent lamps, gas discharge lamps, laser light sources or other types of excitation light sources. A combination of a number of excitation light sources of different or identical type also is contemplated. In some instances, the excitation light source is an excitation light having an excitation wavelength range from about 340 nm to about 380 nm, or at about 360 nm.

The evaluation device can further include at least one data processing device such as, for example, at least one microcomputer. The evaluation device also can include one or more volatile and/or nonvolatile data stores. In some instances, the evaluation device can be configured to draw a conclusion on the presence of the analyte in the sample and/or on a concentration of the analyte in the sample from the variable property recorded during the analyte measurement. Accordingly, the evaluation device can include one or more evaluation functions, which can be implemented programmatically, and by means of which a conclusion can be drawn on the analyte concentration from the recorded property of the test chemical such as, for example, a spectral property, a color change, a reflectance or other properties.

The evaluation device also can perform the consideration described above of the quality of the test chemical in the calculation of the concentration of the analyte in the sample from the recorded property. Thus, the at least one correction, which takes into account the quality of the test chemical, can be implemented in the evaluation device by one or more correction factors and/or one or more correction functions stored in the evaluation device. In this manner, the evaluation device can include an electronic table, in which one or more correction functions and/or one or more correction factors for correction of the analyte concentration corresponding to the recorded quality can be stored.

Furthermore, the evaluation device also can compare the quality with at least one condition, in particular to compare the quality with at least one threshold value. As above, certain actions can be made dependent on the result of the comparison such as, for example, the evaluation of an analyte measurement that has already taken place and/or the release of an analyte measurement that is still to take place and/or the issue of a warning or information to a user and/or to a further apparatus.

Generally, the analytical apparatuses can be equipped by means of a corresponding programmatic facility of the evaluation device to carry out at least one action according to the recorded quality. In particular, at least one action can be carried out such as, for example, an output of a message to a user such as a warning message; a dissemination of at least one item of information about the quality to at least a further device such as an external computer and/or a medical computer; storage of at least one item of information about the quality in at least one data store; prevention or facilitation of the analyte measurement such as an analyte measurement still not carried out; and/or a consideration or non-consideration of an analyte measurement already carried out.

The analytical apparatuses also can include at least one test element, which has at least one test chemical in the form of one or more of the test fields. The test chemical changes at least one property in the presence of the analyte. In some instances, the test element is integrated firmly in the analytical apparatus, but alternatively can be added removably to the analytical apparatus in the form of one or more test elements, which can be present in magazined form in the analytical apparatus.

In some instances, the test chemical can be at least one enzyme such as an oxidase (e.g., a glucose oxidase) or a dehydrogenase (e.g., a glucose dehydrogenase). The test chemical also can include other substances such as, for example, one or more coenzymes and/or one or more mediators and/or one or more dyes. In other instances, the test chemical includes a combination of glucose dehydrogenase and cNAD, as well as optionally at least one dye.

If a test chemical is used that includes at least one enzyme, the quality can then be at least one item of information about an activity of the enzyme. The activity of an enzyme is a measure of how rapidly a starting material reacted by the enzyme is converted to products. The activity can refer here to the entire test chemical, a part thereof, or only to the enzymes. Thus, for example, the rate of a reaction of the analyte to be detected can be determined and therefrom a rate constant.

The test chemical can be at least largely stable to environmental influences such as heat and humidity. In some instances, the test chemical can be present as a dry chemical. For example, for the test a test strip or another type of test element containing the test chemical can be prepared, using a customary method the enzyme activity of an enzyme of the test chemical can be measured, then the storage described above can be carried out and subsequently again the same method for measurement of the enzyme activity can be carried out. This procedure is customarily carried out using a representative collective of test elements or test chemicals. Alternatively or additionally to a stability to environmental influences in the form of atmospheric humidity, a high stability of the test chemical to environmental influences in the form of radiation customarily used overall for a sterilization of the analytical auxiliaries and/or of the analytical magazines can preferably also be given, for example, gamma radiation and/or beta radiation and/or another type of ionizing radiation.

The test chemical therefore can include an enzyme and a stable coenzyme, which are stored together. It has been found that with the aid of a stable coenzyme, a long-term stabilization of several weeks or months at high relative humidity or even in liquid phase and at elevated temperatures is possible. This discovery is surprising, as it is known that enzymes in the presence of native coenzyme indeed have an increased short-term stability for some hours, but a lower shelf life over a relatively long period of time. Faced with these discoveries and compared to the art, it was surprising that an enzyme in the presence of a stable coenzyme has a markedly increased long-term stability than an enzyme in the presence of a native coenzyme, in particular as the stable coenzymes have a lower binding constant with the enzyme than the native coenzyme.

The test chemical also can include at least one coenzyme, especially a stable coenzyme. The coenzyme can be a coenzyme modified chemically to have a higher stability (e.g., hydrolytic stability) when compared to a native coenzyme. The coenzyme is stable to hydrolysis under test conditions. When compared to the native coenzyme, the stable coenzyme also can have a lower binding constant for the enzyme, for example, a binding constant lowered by a factor of two or more. In some examples, the stable coenzyme is carbaNAD (cNAD).

The modification of the stable coenzyme by reaction with the analyte can in principle be detected in any desired manner. Here, any known method of detecting an enzymatic reaction can be employed. In some instances, the modification of the stable coenzyme is detected by optical methods. Optical detection methods, include measuring a reflectance, an absorption, a fluorescence, a circular dichroism (CD), an optical rotation dispersion (ORD), refractometry, photometry or combinations thereof. In some instance, the optical detection method is photometry. Photometry may require presence of at least one mediator, which increases the reactivity of the reduced coenzyme and makes possible a transfer of electrons to a suitable optical indicator or an optical indicator system. Accordingly, the test chemical also can include at least one such mediator.

Furthermore, the test chemical can contain at least one indicator such as an optical indicator.

The modification of the coenzyme by measurement of the fluorescence is particularly preferably detected. The fluorescence measurement is highly sensitive and makes possible the detection even of low concentrations of the analyte in miniaturized systems.

Alternatively, the modification of the coenzyme also can be detected electrochemically using a suitable test element such as, for example, an electrochemical test strip. A prerequisite for this is in turn the use of suitable mediators, which can be converted to a reduced form by the reduced coenzyme by transfer of electrons. The determination of the analyte is carried out by means of a measurement of the current needed for reoxidation of the reduced mediator, which correlates with the concentration of the analyte in the sample.

For detecting an analyte, a test element can be used for a liquid test, the test chemical being present in the form of a solution or suspension in an aqueous or non-aqueous liquid or as a powder or lyophilizate. However, a test element also can be used with a dry test where the reagent is applied to a carrier element, in particular a carrier strip or test carrier tape. The carrier can include a test strip having an absorbent or/and swellable material, which is wetted by the sample liquid to be investigated.

In some instances, the test format includes using glucose dehydrogenase with a stable NAD derivative for detecting glucose, a derivative of the reduced coenzyme NADH being formed. The detection of NADH is carried out by optical methods. An exemplary test system is described in US Patent Application Publication No. 2005/0214891.

With respect to the test chemical, it can be stably designed such that this comprises an enzyme stabilized with a stable coenzyme, where the stabilized enzyme, in the case of storage for at least about two weeks, at least about four weeks, and at least about eight weeks at a temperature of at least about 20° C., at least about 25° C. and at least about 30° C., if appropriate at high atmospheric humidity and without drying reagent, shows a decrease in the enzymatic activity of less than about 50%, less than about 30% and less than about 20% when compared with a starting value.

The test chemical can be contained in a test element in any desired manner. The test chemical or the test element can be suitable for carrying out dry or liquid tests. For example, the test chemical can be applied to a suitable carrier material such as, for example, a plastic material, a ceramic material and/or a paper material.

In view of the foregoing, methods also are provided for detecting at least one analyte in a sample. The methods can be carried out using an analytical apparatus as described herein. The methods include the following steps, which do not necessarily have to be carried out in the order shown. Furthermore, individual, multiple or all the method steps can also be carried out repeatedly, and several method steps can be carried out overlapping in time or simultaneously.

One step includes performing a quality measurement on the test chemical. The quality of the test chemical, on which a conclusion is drawn in the quality measurement, can include at least one item of information about an activity of the at least one enzyme and/or one coenzyme optionally contained in the test chemical. The quality can directly be the activity of the enzyme or coenzyme or can be or include other information, which is derived from the activity of the enzyme or coenzyme or from which the activity of the enzyme or coenzyme can be concluded.

For example, during the quality measurement an item of information such as, for example, at least an intrinsic fluorescence/luminescence can be recorded. From the intrinsic luminescence, a quality of the test chemical is concluded such as a degradation of the test chemical or not. The quality measurement can be carried out using at least one quality detector.

Another step includes measuring at least one analyte. In some instances, in the measuring step at least a property of at least one test chemical of a test element changeable by presence of the analyte is recorded such as, for example, an electrical property and/or optical property. The measuring step can be performed by an analytical apparatus as described herein. Alternatively or additionally, the measuring step can be carried out by a user without use of the analyte detector. Thus, a test element can be used such as, for example, a test strip, test rod or test tape, which contains at least one test chemical, where a user visually detects a discoloration of the test chemical such as, for example, of at least one test field by eye. The user can carry out a comparison with a specified color scale. Such tests are in principle also commercially obtainable.

In another aspect, methods are provided for using a quality detector and/or an analytical apparatus as described herein to avoid analyte measurements using test elements containing degraded test chemical.

In another aspect, methods are provided for using a measurement of an intrinsic luminescence of a test chemical of a test element for detecting degraded test elements.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
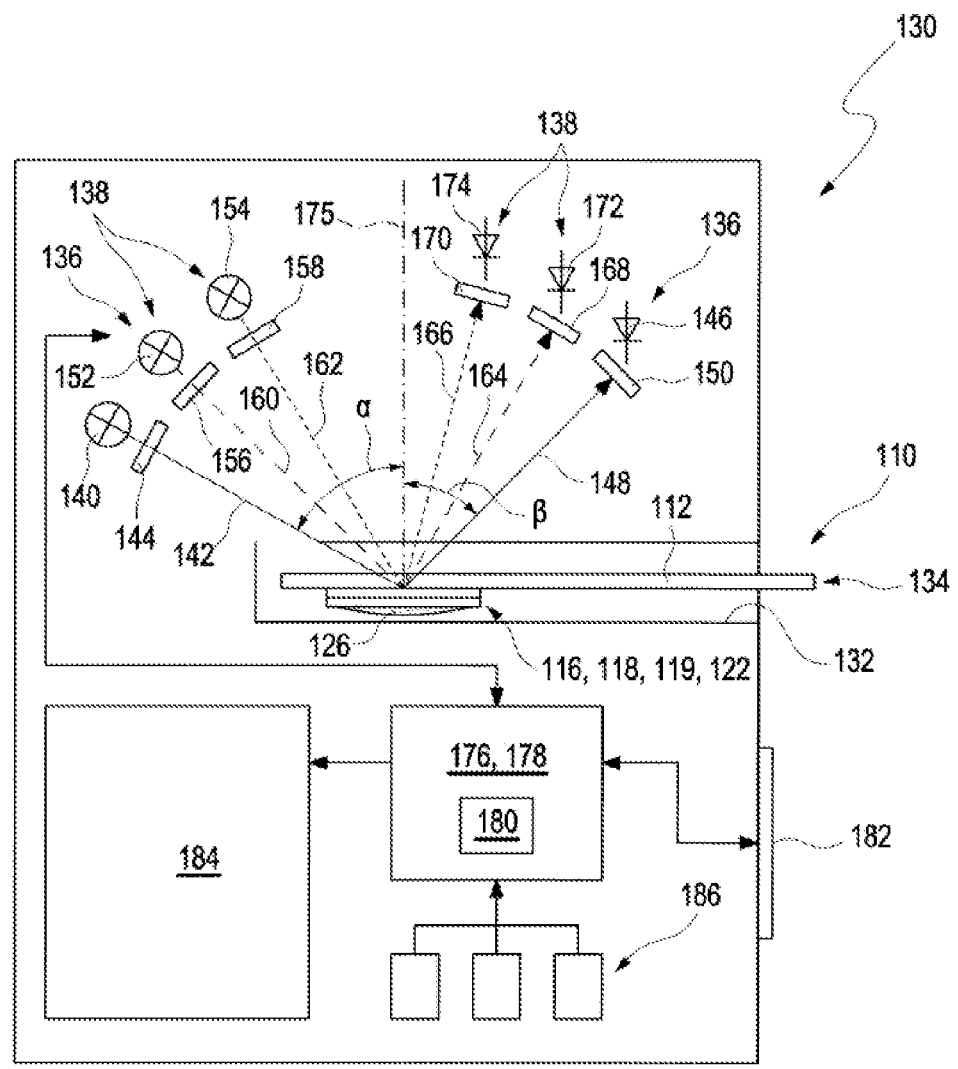
FIG. 1 shows an exemplary analytical apparatus.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The apparatuses and methods now will be described more fully hereinafter with reference to the accompanying drawings, in which some, but not all embodiments of the inventive concept are shown. Indeed, the apparatuses and methods may be embodied in many different forms and should not be construed as limited to the embodiments set forth herein; rather, these embodiments are provided so that this disclosure will satisfy applicable legal requirements.

Likewise, many modifications and other embodiments of the apparatuses and methods described herein will come to mind to one of skill in the art to which the disclosure pertains having the benefit of the teachings presented in the foregoing descriptions and the associated drawings. Therefore, it is to be understood that the apparatuses and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the apparatuses and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may both refer to a situation in which, besides B, no other element is present in A (i.e., a situation in which A solely and exclusively consists of B) or to a situation in which, besides B, one or more further elements are present in A, such as element C, elements C and D, or even further elements.

Overview

Analytical apparatuses and methods of detecting at least one analyte in a sample are disclosed herein incorporate a quality measurement on a test element. That is, they provide a reliable and safe detection of whether a test element—if appropriate, despite high long-term stability—is in a state of disrepair or is degraded to an intolerable extent. As used herein, "detection" means a process in which at least one item of information is generated that allows a qualitative or quantitative conclusion on the presence or non-presence of the analyte in the sample and/or an amount or concentration of the analytes in the sample. This information can be conveyed, for example, directly to a user and/or can be presented in electronic form such as, for example, in a data storage and/or by transfer to an apparatus separate from the analytical apparatus.

Experimental investigations, which are presented below in greater detail by way of example, show that in many cases in the test chemical of test elements that the component of lowest stability is the enzyme, which can degrade and can result in a decrease in enzyme activity.

As used herein, "analyte" means any desired substance or substance combination to be detected qualitatively or quantitatively. As explained above, this at least one analyte, where preferably precisely one analyte or a group of certain analytes are specifically detected, can be in particular at least one substance, which is directly or indirectly involved in a metabolism of a human or animal body. In particular, it can be at least one metabolite. Examples of analytes that can be detected individually or in any desired combination include, but are not limited to, glucose, in particular blood glucose, uric acid, ethanol, lactate and cholesterol. Other analytes, however, are also contemplated.

As used herein, "analyte measurement" means a measuring process in which at least a detectable variable is recorded that serves for the detection of the analyte. For example, the detectable variable can be an optical/physical measured variable such as, for example, an optical measured variable (e.g., a color appearance, a luminescence or a luminescence lifetime) and/or can be an electrochemical variable such as, for example, a voltage and/or a current. Optical and electrochemical detection methods are well known in the art.

For detecting electrical properties, an electrical measuring device can be provided. Examples of electrical measuring devices include, but are not limited to, a voltage measuring device and a current measuring device. For detecting optical properties, at least one optical analyte detector can be used.

As used herein, "quality measurement" means a process in which the quality of the test chemical of a test element is recorded qualitatively or quantitatively.

As used herein, "quality of the test chemical" means at least one item of information about a state of the test chemical. In particular, this at least one item of information can be about an aging condition of the test chemical such as information about a degradation or a degradation state of the test chemical. Thus, the at least one item of information can be of a digital nature and can be displayed as "Quality OK" or "Quality not OK". Such information can be determined with the aid of one or more threshold values. Thus, in the quality measurement at least one quality measurement value can be generated in the form of a corresponding signal and/or in the form of corresponding electronic information, where this at least one quality measurement value is compared with one or more threshold values to generate the information on the quality of the test chemical.

Alternatively or additionally to a purely digital item of information, the item of information also can be a plurality of information so that the quality can be quantified. Thus, for example, the item of information can include at least one item of quality information on a specified scale that quantifies the property of the test chemical such as, for example, a degradation or an aging state.

As used herein, "aging of the test chemical" or "degradation of the test chemical" means any desired change of the test chemical or a part of the test chemical, which can have an influence on the analyte measurement. Examples include, but are not limited to, an undesired oxidation and/or incorporation of water, or physical changes such as so-called conformation changes, crystallizations or similar effects.

Such analytical apparatuses and methods can be employed for detecting one or more analytes in one or more liquid samples such as, for example, body fluids. The at least one sample can in particular be a liquid sample. In particular, it can be a body fluid. For example, the liquid sample can be whole blood, blood plasma, interstitial fluid, saliva, urine or other types of body fluids. Alternatively or additionally to a body fluid, the liquid sample, however, can also be at least one other liquid such as, for example, at least a control solution. Such control solutions can include at least one analyte to be detected in a specified concentration in at least one solvent or solvent mixture in a specified concentration in a solution such as, for example, water.

One field of application, to which the present disclosure is not restricted, is medical diagnosis, in particular, in-vitro diagnosis. Here, one or more analytes, which can be present in a human or animal body, can be detected in a fluid sample taken from the human or animal body. Other areas of application also are possible and may even be outside of medical diagnosis such as, for example, in general analysis or in chemical process technology.

When compared to the methods described in EP Patent Application Publication Nos. 1189064 and 2221608, the analytical apparatuses and methods disclosed herein do not depend on recording a dry blank value. A dry blank value measurement of a reflectance for the exclusion of coarsely degraded test elements, however, optionally can be provided. The proposed methods, in which the intrinsic luminescence of the test chemical, such as an intrinsic fluorescence of at least one enzyme and/or coenzyme optionally contained in the test chemical is recorded, makes possible a considerably more precise recording of degradation processes, which can relate directly to the component involved in the analyte detection or the components involved in the analyte detection. By recording of the intrinsic luminescence, which can take place in at least two different wavelength regions, an internal referencing of the method can be realized. In this manner, by quotient forming or other evaluating methods, a referencing to a batch control value that is complicated to attach can be avoided, although such a referencing is optional additionally feasible. Advantageously, a batch of test elements such as, for example, a batch of test strips or a tape cassette need not have added to them a data store that contains the batch control value. Overall, the methods disclosed herein are considerably safer and simpler to design when compared known methods.

As used herein, "intrinsic luminescence" means a luminescence of the test chemical that is a phosphorescence and/or a fluorescence, which can be emitted by the test chemical, possibly with interaction with further elements of the test element such as the carrier element, if no sample is applied to the test chemical. Such an intrinsic luminescence can be recorded, for example, before applying the sample to the test chemical. For recording intrinsic luminescence, the test chemical can be irradiated with excitation light having one or more wavelengths, and the luminescence resulting therefrom can be recorded, simultaneously with or without a time delay of the irradiation, by means of a suitable detector. In particular, the intrinsic luminescence can be an intrinsic fluorescence of the test chemical. Intrinsic luminescence therefore can include an intrinsic fluorescence of the test chemical and can be resolved spectrally and/or recorded integrally over a wavelength range.

According to the present disclosure, simple, practicable and nondestructive methods of detecting aging of test elements are thus provided, particularly for detecting enzyme degradation. The quality measurement can be performed directly, as by means of the luminescence measurement of enzyme degradation in contrast to indirect methods. Furthermore, the luminescence measurement, as a rule, necessitates no modification of a test chemical formulation.

An initially surprising property of customary test chemicals was found, namely that with a degradation in enzymatic detection reactions, a change in the intrinsic luminescence and in particular in the intrinsic fluorescence of the test chemical is associated before wetting. The examples below are based upon an increased autofluorescence of glucose dehydrogenase. This changed intrinsic luminescence can be used as described herein to determine test element degradation or generally for quality determination of the test chemical or of the entire test element.

Although in the context of the present disclosure, a main focus lies in a detecting degradation on glucose testing elements, the inventive concept incorporated into the proposed analytical apparatuses and methods can be extendable to a multiplicity of test elements and optionally also to a decay recognition in general of test systems (e.g., reagent kits).

The use of fluorophores for detecting glucose concentrations in test strips is generally known in, for example, EP Patent No. 1780288 and Int'l Patent Application Publication No. WO 2009/015870. Glucose-induced changes in the fluorescence of proteins and other fluorophores also are known. See, Pickup et al. (2005) *Biosens. Bioelectron.* 20:2555-2565. Accordingly, it is to be described as surprising in the context of the present disclosure that generally it was found that luminescence changes, in particular fluorescence changes, are observable that can be attributed directly not to detecting the analyte but to degrading and in particular decreasing enzyme activity and correlate with this decrease. Also in Moore et al. (2004), supra, it is disclosed that the lifetime of alcohol dehydrogenase with respect to its activity is determined, in this case by adding NAD+, where here, however, the fluorescence of the coenzyme NADH first formed in the actual analyte detection reaction is measured, not that of the protein itself. In this regard, a wetting of the test chemical with the sample is already necessary to be able to carry out the quality measurement, in contrast to the arrangement herein, in which the intrinsic luminescence of the test chemical is recorded. Thus, in the context of the present disclosure, timely detecting degradation of a test chemical is possible before the test element is brought into contact with the sample, so that a repeated sample generation by perforation of an area of skin with detection of degraded test elements can be avoided in a timely manner. A considerable gain in comfort results for the user of the test elements.

Overall, the methods and analytical apparatuses disclosed herein can be designed safely and nevertheless simply and which can reliably prevent a use of degraded test elements. In this manner, operational safety can be markedly increased, and the risk of an erroneous diagnosis from using compromised/degraded test strips can be markedly decreased.

Test Elements

Figure 8:
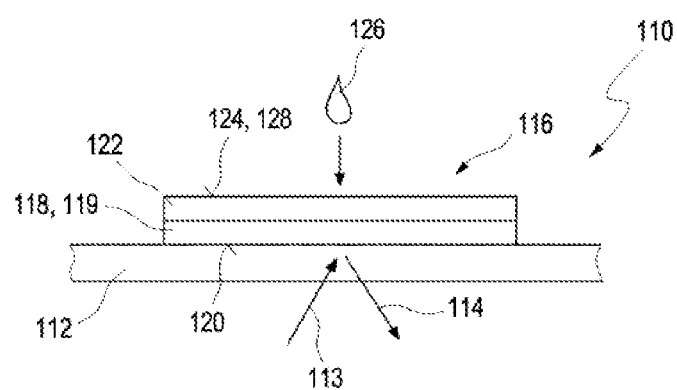
FIG. 8 shows a schematic representation of a layer structure of a test element.

FIG. 8 shows a cross-sectional view of an exemplary test element that can be used in the context of the present disclosure. As used herein, "test element" means an element including at least one test chemical and in some instances can consist exclusively of the test chemical as a detection reagent. In other instances, the test element also can include at least one carrier element, to which the at least one test chemical is applied and/or in which the at least one test chemical is incorporated. The at least one carrier element can be produced wholly or partially from a material including, but not limited to, a plastic material, a paper material, a ceramic material and/or a laminate material. The test element also can include at least one test field, in which the test chemical can be applied to the carrier element and/or incorporated in the carrier element.

As used herein, "test chemical" means a substance or a substance mixture that, in the presence of the analyte, changes at least one detectable changeable property such as, for example, a physically detectable property. Thus, the test chemical can change at least one property dependent on the presence of the analyte. For example, the at least one property can change between two states, where one state occurs if the analyte is present, and another state occurs if the analyte is absent. Alternatively or additionally, the at least one property can change stepwise or continuously, where the property can assume several states depending on a concentration of the analyte such as, for example, by the property being a function of the concentration of the analyte.

In some instances, the test chemical can be at least one enzyme that is stabilized long-term. As used herein, "stabilized long-term" means an enzyme stabilized with a stable coenzyme (e.g. as a dry substance) that can be stored over a period of at least about two weeks, of at least about four weeks, or of at least about eight weeks and where the enzyme activity preferably decreases by less than about 50%, less than about 30%, or less than about 20% with respect to the starting value of the enzyme activity.

Furthermore, the test chemical can be designed in such a way that the enzyme stabilized with at least a stable coenzyme can be stored at elevated temperatures such as, for example, at a temperature of at least about 20° C., of at least about 25° C., or of at least about 30° C. In view thereof, the enzyme activity decreases by less than about 50%, less than about 30%, or less than about 20% with respect to its starting value.

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

By stabilization, it is possible to store the enzyme stabilized with a stable coenzyme even without drying reagent for a long time, as indicated above, and/or at high temperatures, as indicated above. Furthermore, the stabilized enzyme can be stored at a high relative air humidity (e.g., a relative air humidity of at least about 50%) where the enzyme activity decreases by less than about 50%, less than about 30%, and less than about 20% with respect to the starting value.

The storage of the enzyme stabilized with a stable coenzyme can on the one hand take place as a dry substance or on the other hand in liquid phase. In some instances, the storage of the stabilized enzyme takes place on or in a test element, which is suitable for determination of an analyte. The enzyme stabilized with a stable coenzyme is a constituent of the test chemical, which optionally can additionally contain other constituents such as, for example, salts, buffer, etc. In other instances, the test chemical is free of a mediator.

In some instances, the test chemical can be at least largely stable to environmental influences such as moisture. As used herein, "test chemical essentially stable to environmental influences" means a test chemical that is stable to atmospheric moisture and advantageously likewise to an increased temperature and/or to irradiation with ultraviolet light and/or to sterilization processes, in particular sterilization processes using ionizing radiation. Generally, the test chemical is stable if storage at about 32° C., a relative humidity of about 85% at normal pressure over a period of three weeks decreases the activity, for example, the enzyme activity of the test chemical of the analytical auxiliary, by less than about 50%, by less than about 30%, or by less than about 20%. The activity can be determined here by means of any method known in the art, as in the context of the given definition only a ratio of the decrease of the activity measured using this method to an activity measured using this method before storage or immediately after the preparation of the analytical auxiliary is of relevance. The activity can refer here to enzyme activity of a dry chemical, in particular in a test strip. For example, methods are known in which one extracts the enzyme from the test chemical or the test strip and then determines the activity, for example, by means of an ultraviolet absorption. See, e.g., Bergmeyer (1970) "Methoden der enzymatischen Analyse," Verlag Chemie, 2$^{nd}$ ed. p. 417; and Banauch et al. (1975) Z. Klin. Chem. Klin. Biochem. 13:101-107.

As an example of such a test chemical stable to environmental influences, reference can be made to Int'l Patent Application Publication No. WO 2007/012494. See also, EP Patent No. 0821234; and Int'l Patent Application Publication Nos. WO 2007/012494 and WO 2010/094632. The test chemical can be used alone or alternatively in combination with one or more other test chemicals. Alternatively or additionally, the test chemical can also be designed as described in EP Patent Application Publication Nos. 1780288 and 2093284; US Patent Application Publication No. 2007/0026476; Int'l Patent Application Publication Nos. WO 2009/015870, WO 2009/103540, WO 2010/052306, WO 2010/052307 and WO 2010/094426; and Hones et al. (2008) Diabetes Technol. Ther. 10:10-26. Other types of stable test chemicals alternatively or additionally can be used such as, for example, the test chemical described in Int'l Patent Application Publication No. WO 2007/012494.

As noted above, the test chemical can be incorporated as a detection reagent into a detection layer having other components. As used herein, "detection reagent" means a chemical substance or a chemical substance mixture, which in the presence of the at least one analyte changes at least a detectable property, in particular a physically and/or chemically detectable property. Typically, the property change takes place specifically exclusively in the presence of the at least one analyte to be detected, not, however, in the presence of other substances. However, in practice, a non-specific property change can be tolerated to a certain extent in the presence of other chemical substances, the presence of which in the sample of the body fluid is as a rule improbable and/or which only are present in very low concentrations.

Thus, in addition to the test chemical, the detection layer 118 can include a coenzyme, especially stable coenzymes. Examples of stable coenzymes include stable derivatives of nicotinamide adenine dinucleotide (NAD/NADH) or nicotinamide adenine dinucleotide phosphate (NADP/NADPH), or shortened NAD derivatives (e.g., without AMP part or with non-nucleosidic radicals such as hydrophobic radicals). Stable coenzymes also can be a compound of formula (I):

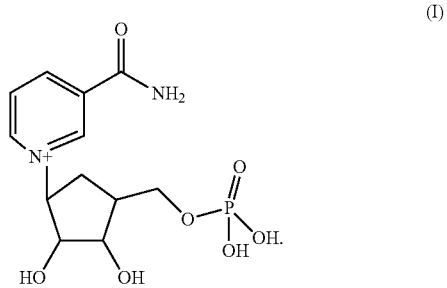 [SMILES: NC(=O)c1ccc[n+](C2CC(COP(=O)(O)O)C(O)C2O)c1]

(I)

Additional examples of stabilized coenzymes are disclosed in Int'l Patent Application Publication No. WO 2007/012494 and U.S. patent application Ser. No. 11/460,366.

The stable coenzyme also can be a compound of the general formula (II):

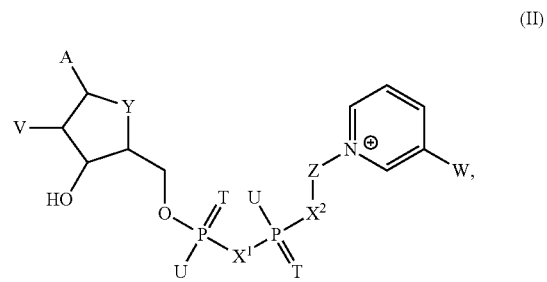

(II)

where:
A=adenine or an analog thereof,
T=in each case independently O, S,
U=in each case independently OH, SH, BH$_3^-$, BCNH$_2^-$,
V=in each case independently OH or a phosphate group, or two groups, which form a cyclic phosphate group;
W=COOR, CON(R)$_2$, COR, CSN(R)$_2$ where R=in each case independently H or C$_1$-C$_2$-alkyl,
X$^1$, X$^2$=in each case independently O, CH$_2$, CHCH$_3$, C(CH$_3$)$_2$, NH, NCH$_3$,
Y=NH, S, O, CH$_2$,
Z=is a linear or cyclic organic radical, with the proviso that Z and the pyridine radical are not linked by a glycosidic compound, or a salt or optionally a reduced form thereof.

In some instances, Z can be a linear radical having 4-6 C atoms, 4 C atoms, wherein 1 or 2 C atoms optionally are replaced by one or more heteroatoms selected from O, S and N, or a radical including a cyclic group having 5 or 6 C atoms, which optionally contains a heteroatom selected from O, S and N, as well as optionally one or more substituents, and a radical $CR^4_2$, where $CR^4_2$ is bonded to the cyclic group and to $X^2$, where $R^4$=in each case independently H, F, Cl, $CH_3$.

In other instances, Z is a saturated or unsaturated carbocyclic or heterocyclic five-membered ring, in particular a compound of the general formula (III):

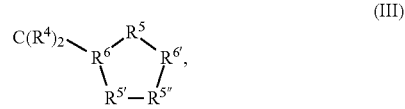

(III)

where a single or double bond can be present between $R^{5'}$ and $R^{5'''}$,
where $R^4$=in each case independently is H, F, Cl, $CH_3$, $R^5$=$CR^4_2$,
where $R^{5'}$=O, S, NH, $NC_1$-$C_2$-alkyl, $CR^4_2$, CHOH, $CHOCH_3$, and $R^{5'''}$=$CR^4_2$, CHOH, $CHOCH_3$, if a single bond is present between $R^{5'}$ and $R^{5'''}$, and
where $R^{5'}$=$R^{5'''}$=$CR^4$, if a double bond is present between $R^{5'}$ and $R^{5'''}$, and $R^6$, $R^{6'}$=in each case independently CH or $CCH_3$.

In some instances, the compounds include adenine or adenine analogs, like, for example, $C_8$- and $N_6$-substituted adenine, deaza variants like 7-deaza, aza variants like 8-aza or combinations like 7-deaza or 8-aza or carbocyclic analogs, like formycin, where the 7-deaza variants can be substituted in the 7-position by halogen, $C_1$-$C_6$-alkinyl, -alkenyl or -alkyl.

In other instances, the compounds include adenosine analogs, which instead of ribose contain, for example, 2-methoxydeoxyribose, 2'-fluorodeoxyribose, hexitol, altritol or polycyclic analogs, like bicyclo, LNA and tricyclo sugars.

In the compounds of the general formula (II), (di-)-phosphate oxygens can be isotronically replaced, like e.g. $O^-$ by $S^-$ or $BH_3^-$, O by NH, $NCH_3$ or $CH_2$ and =O by =S.

In the compounds of the general formula (II), W can be $CONH_2$ or $COCH_3$.

In the groups of the general formula (III), $R^5$ can be $CH_2$. $R^{5'}$ can be selected from $CH_2$, CHOH and NH. In some instances, $R^{5'}$ and $R^{5'''}$ are in each case CHOH. In other instances, $R^{5'}$ is NH and $R^{5'''}$ $CH_2$.

In addition to the test chemical 119, the detection layer 118 can include additional components such as mediators and/or indicators. Examples of mediators include, but are not limited to, nitrosoanilines such as [(4-nitrosophenyl)imino]dimethanol hydrochloride; quinones such as phenanthrenequinones, phenanthrolinequinones or benzo[h]-quinolinequinones; phenazines such as 1-(3-carboxypropoxy)-5-ethylphenazinium trifluoromethanesulfonate; and/or diaphorase (EC 1.6.99.2). Examples of phenanthrolinequinones include, but are not limited to, 1,10-phenanthroline-5,6-quinones, 1,7-phenanthroline-5,6-quinones, 4,7-phenanthroline-5,6-quinones and their N-alkylated or N,N'-dialkylated salts, where in the case of N-alkylated or N,N'-dialkylated salts, halides, trifluoromethanesulfonate or other anions increasing the solubility are used as a counterion.

As used herein, "indicator" means any desired substance that is influenced by the course of the detection reaction of the analyte detection, in particular of the enzymatic reaction, such that at least one property change of the indicator can be recorded in the course of the detection reaction. In some instances, this property can be an optical property. Thus, the indicator can be at least one dye.

As the optical indicator or as the optical indicator system, in particular, any desired substance can be used that is reducible and during reduction undergoes a detectable change of its optical properties such as, for example, color, fluorescence, reflectance, transmission, polarization or/and refractive index. The determination of the presence or/and of the amount of the analyte in the sample can take place using the naked eye or/and by means of a detection device using a photometric method appearing suitable to one of skill in the art. In some instances, heteropolyacids such as 2,18-phosphormolybdic acid are used as optical indicators, which are reduced to the corresponding heteropolyblue.

Regardless of whether the test chemical is used alone or in combination with other components as a detection reagent, the test chemical can be arranged on the test element as a test field. As used herein, "test field" means an area to which at least a cohesive layer of the test chemical is applied to the carrier element or incorporated into the carrier element. In some instances, the test element can include one or more such test fields. The test fields can be arranged next to one another on the carrier element or in the carrier element. The carrier element can be strip-like, disk-shaped or tape-shaped.

Referring again to FIG. 8, an exemplary test element 110 includes a carrier element 112. A plastic film such as a polycarbonate (e.g., Pokalon®) can be used as the carrier element. Overall, the test element 110 can be designed as test strips or a test tape. The carrier element 112 can be designed to be completely or partially transparent so that irradiated light 113 and detectable light 114 can penetrate the carrier element 112.

In some instances, a layer structure can be applied to the carrier element 112. As shown in FIG. 8, two layers form a test field 116, where the test field 116 includes a detection layer 118 including a test chemical 119 and having a detection side 120 facing the carrier element 112. Furthermore, the test field 116 optionally includes a separating layer 122 on a side of the detection layer 118 facing away from the carrier element 112. This separating layer 122 separates interfering constituents of a sample 126 of, for example, a body fluid applied to a sample application side 128 on a test field surface 124, for example, for separating erythrocytes.

In other instances, the test element 110 can include several detection layers 118, several separating layers 122, or no separating layer 122 at all. Furthermore, the test element 110 can be supplemented with various other elements such as, for example, a spreading net. Additionally, parts of the test field surface 124 can be covered with a hydrophobic material to make only one part of the sample application side 128 accessible for a loading with the sample 126.

In some instances, the test element 110 can be constructed as disclosed in EP Patent No. 0821234 or to other known test element configurations.

As noted above, the test element can be a layer structure, where the at least one test chemical 119 is applied to the carrier element 112 in the form of one or more test chemical layers. For example, the at least one other layer can be a reflection layer of one or more pigments that have reflective properties such as, for example, white pigments such as titanium dioxide particles. In some instances, the at least one reflection layer can be on a surface of the carrier element 112 that faces away from the test chemical 119, thus serving as the sample application side 128. In this manner, the detection of the at least one analyte can take place through the carrier element from a side opposite to the sample application side 128. To facilitate this design, the carrier element 112 can be completely or partially optically transparent for at least one excitation light irradiated into the test chemical and/or transparent for at least one detection light reflected and/or emitted by the test chemical, where a transparency is understood as a transparency of at least about 70%. In other instances, the liquid sample can be introduced laterally into the test chemical (i.e., parallel to the layer structure).

In many cases, the test chemical 119 includes at least one enzyme and/or uses at least an enzymatic detection. For example, in such an enzymatic detection charge carriers can be generated, which, for example, can be transferred to one or more indicator dyes or which can be detected directly or indirectly electrochemically. Thus, for example, enzymatic detection reactions are known, in which charge carriers are transferred to reaction equivalents, which can be formed, for example, transiently in the detection reaction in an amount equivalent or corresponding to the reaction of the analyte. These reaction equivalents and/or their charge carriers can be detected, for example, by means of electrochemical detection reactions, or in turn a transfer of charges to corresponding indicators can take place, for example dyes, such that, for example, a color change can be observed. Examples of enzymatic detection reactions, which can also be employed in the context of the present disclosure in the test chemical, are described in Hönes et al. (2008), supra.

The test chemical 119 therefore can include at least one enzyme, especially a stabilized enzyme such as a coenzyme-dependent enzyme. Examples of the at least one enzyme include, but are not limited to, glucose dehydrogenase (E.C.1.1.1.47), lactate dehydrogenase (E.C.1.1.1.27, 1.1.1.28), malate dehydrogenase (E.C.1.1.1.37), glycerol dehydrogenase (E.C.1.1.1.6), alcohol dehydrogenase (E.C.1.1.1.1), alpha-hydroxybutyrate dehydrogenase, sorbitol dehydrogenase or amino acid dehydrogenase, such as, for example, L-amino acid dehydrogenase (E.C.1.4.1.5). Other examples of the at least one enzyme include, but are not limited to, glucose oxidase (E.C.1.1.3.4); cholesterol oxidase (E.C.1.1.3.6); aminotransferases such as, for example, aspartate or alanine aminotransferase, 5'-nucleotidase or creatine kinase; glucose 6-phosphate dehydrogenase (EC 1.1.1.49); NAD-dependent cholesterol dehydrogenase (EC 1.1.1.62); FAD-dependent glucose dehydrogenase (EC 1.1.99.10); PQQ-dependent glucose dehydrogenase (EC 1.1.5.2). In some instances, the enzyme is glucose dehydrogenase. In other instances, and as noted above, the enzyme can be a mutant and can even be a stabilized enzyme.

As used herein, "dehydrogenase" means polypeptides that catalyze a reaction of a substrate by transfer of hydrides (H$^-$) as redox equivalents to an acceptor molecule, such as a redox cofactor. As used herein, "redox cofactor" means a molecule that can serve as an acceptor for enzymatically transferred redox equivalents, and in particular to hydrides (H$^-$). Examples of dehydrogenases include, but are not limited to, glucose dehydrogenase (E.C.1.1.1.47); lactate dehydrogenase (E.C.1.1.1.27, 1.1.1.28); malate dehydrogenase (E.C.1.1.1.37); glycerol dehydrogenase (E.C.1.1.1.6); alcohol dehydrogenase (E.C.1.1.1.1); alpha-hydroxybutyrate dehydrogenase; sorbitol dehydrogenase; amino acid dehydrogenase, in particular L-amino acid dehydrogenase (E.C.1.4.1.5); glucose oxidase (E.C.1.1.3.4); cholesterol oxidase (E.C.1.1.3.6); aminotransferases, in particular aspartate or alanine aminotransferase; 5'-nucleotidase; creatine kinase; glucose 6-phosphate dehydrogenase (EC 1.1.1.49); NAD-dependent cholesterol dehydrogenase (EC 1.1.1.62); FAD-dependent glucose dehydrogenase (EC 1.1.99.10); and PQQ-dependent glucose dehydrogenase (EC 1.1.5.2).

Dehydrogenases can depend on a redox cofactor, which sometimes is designated as a coenzyme. Examples of redox cofactors include, but are not limited to, pyrroloquinolinequinine (PQQ); nicotinamide adenine dinucleotide (NAD) or a derivative thereof; a flavine, in particular flavine adenine dinucleotide (FAD); and flavine mononucleotide (FMN).

Mutants of the at least one enzyme also can be used and also are suitable as stabilized enzymes. As used herein, "mutant" means a genetically modified variant of a native enzyme. The genetically modified variant of the native enzyme can differ in at least one amino acid from the wild-type enzyme. The genetically modified variant of the native enzyme can have an equal number of amino acids or a different number of amino acids when compared to the wild-type enzyme. The mutant also can include at least one deletion, at least one substitution and/or at least one insertion. Thus, a mutant can be understood as meaning a genetically modified variant of a native enzyme, which when compared to the wild-type enzyme, has a sequence homology of at least about 80%, at least about 90%, or at least about 95%. Here, sequence homology is understood as meaning sequence identity. Homology or identity can be determined in a comparison window, which extends over the entire length of the amino acid sequences to be compared, arranged optimally with respect to one another. Likewise, the calculation can take place in a comparison window, which extends over a subregion of the amino acid sequences to be compared, arranged optimally with respect to one another. The subregion should include at least half of the total number of amino acids of the lengths of the two amino acid sequences. For determining the sequence identity (in percent), the number of identical amino acids in the comparison window is divided by the total number of the amino acids of the two sequences to be compared in the comparison window and multiplied by 100. Two amino acid sequences can be arranged optimally with respect to one another by means of algorithms known in the prior art for amino acid sequence comparisons. An example is the BLASTP algorithm, which can be employed using the standard specified parameters.

Regardless of the mutation, the mutant has essentially the same activity as the native enzyme. Mutants of the aforementioned native enzymes should preferably, moreover, be encoded by nucleic acid molecules, which are in the position to hybridize with the nucleic acid molecules under stringent hybridization conditions, which encode the abovementioned native enzymes. As used herein, "stringent hybridization conditions" means a hybridization in which the nucleic acids to be hybridized are incubated at about 65° C. in Church buffer (0.5 M NaPO$_4$ (pH 7.15), 7% SDS; 1 mM EDTA) for about 12 hours and subsequently washed twice for about 30 min in wash buffer (40 mM NaPO$_4$ (pH 7.15), 1% SDS; 1 mM EDTA). One of the nucleic acids to be hybridized is immobilized here, the other is provided with a detectable label. If the nucleic acids hybridize with one another, this hybridization can be detected by means of the detectable label on the immobilized nucleic acid. Methods of carrying out hybridization reactions are known in the art.

Mutations can be introduced site-specifically or non-site-specifically using recombinant methods known in the art, where, according to the respective requirements and conditions, at least one amino acid exchange results within the amino acid sequence of the native enzyme. In some instances, the mutant has an increased thermal or hydrolytic stability compared to the wild-type enzyme.

When the mutant is a mutated glucose dehydrogenase, it can contain the amino acid(s) modified compared to the corresponding wild-type glucose dehydrogenase in principle in any desired position of its amino acid sequence. In some instances, the mutated glucose dehydrogenase includes a mutation in at least one of positions 96, 170 and 252 of the amino acid sequence of the wild-type glucose dehydrogenase, where mutants with mutations in position 96 and position 170 or mutations in position 170 and position 252 are advantageous. In other instances, the mutated glucose dehydrogenase contains no further mutations besides these mutations.

The mutation in the positions 96, 170 and 252 include any desired amino acid exchange that leads to a stabilization (e.g., an increase in the thermal or hydrolytic stability of the wild-type enzyme). In some instances, the mutation in position 96 is an amino acid exchange of glutamic acid for glycine. In some instances, the mutation in position 170 is an amino acid exchange of glutamic acid for arginine or lysine, in particular an amino acid exchange of glutamic acid for lysine. In some instances, the mutation in position 252 is an amino acid exchange of lysine for leucine.

The mutated glucose dehydrogenase can be obtained by mutating a wild-type glucose dehydrogenase originating from any desired biological source. As used herein, "biological source" means both prokaryotes, such as, for example, bacteria, and eukaryotes, such as, for example, mammals and other animals. In some instances, the wild-type glucose dehydrogenase originates from a bacterium such as, for example, *Bacillus megaterium, Bacillus subtilis* or *Bacillus thuringiensis*. In other instances, the mutated glucose dehydrogenase is obtained by mutating wild-type glucose dehydrogenase from *B. subtilis* (e.g., GlucDH_E96G_E170K or GlucDH_E170K_K252L).

The test elements therefore produce at least one property change that can be, for example, an optically detectable property such as a color change. Test elements containing optical detection reagents are adequately known from the art.

Analytical Apparatuses

Figure 7:
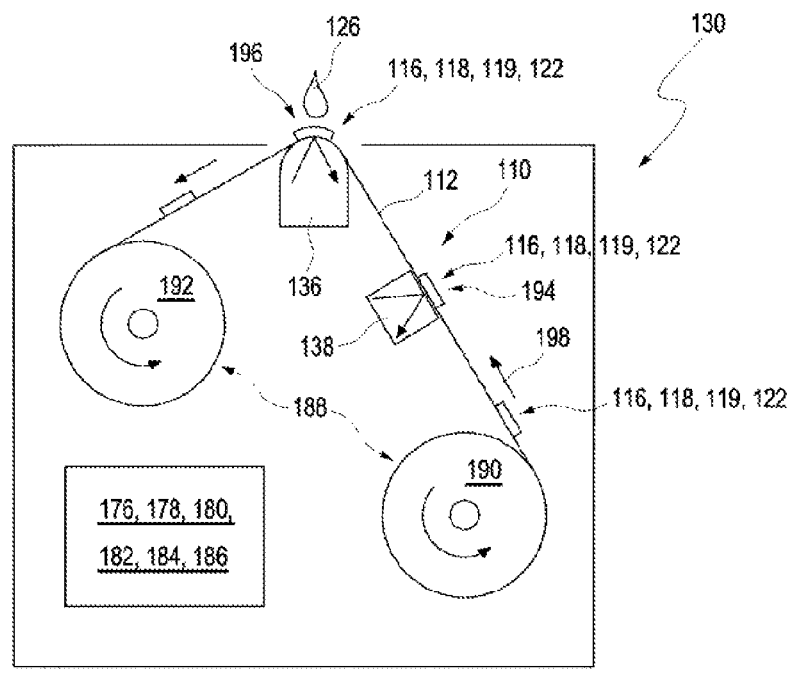
FIG. 7 shows another exemplary analytical apparatus.

Analytical apparatuses are provided that incorporate the inventive concept. FIGS. 1 and 7 show two different exemplary embodiments of analytical apparatuses 130. In FIG. 1, test elements 110 are used in the form of test strips, and in FIG. 7 test elements 110 are used in the form of a test tape. It may be pointed out that numerous other embodiments are possible and that the figures only show the mode of action of the analytical apparatuses 130 in highly schematic form.

The analytical apparatus 130 shown in FIG. 1 includes an insertion slot 132 through which the test element 110 can be pushed into the analytical apparatus 130. An alternative arrangement is contemplated in which several test elements 110 in the form of test strips are added to the analytical apparatus 130 in magazines such as, for example, a bar magazine, a stacking magazine or a drum magazine. The test element 110 can be designed as depicted in FIG. 8 and can include, for example, a test field 116 with a detection layer 118 containing the test chemical 119 and optionally a separating layer 122. Placing of a sample 126, which is not depicted in FIG. 1, can take place directly on the test field 116 or can take place by means of an application position 134 at an end of the test element 110 projecting from the insertion slot 132, followed by capillary transport to the test field 116. Such test elements 110 are known in the art.

The analytical apparatus 130 shown in FIG. 1 also includes at least one analyte detector 136 and at least one quality detector 138, which are only shown schematically. It may be pointed out that the arrangement shown in FIG. 1 without, for example, the analyte detector 136 and exclusively with the quality detector 138, also can serve as an exemplary embodiment of a quality detector, which can be used separately and without the analyte detector 136, independently of a subsequent analyte measurement, to check the quality of test strips.

For example, in this way the quality of individual test strips can be checked for a visual analyte detection with the aid of a specified color scale. Other embodiments also are possible.

The analyte detector 136 can include an analyte light source for irradiating of the test chemical 119 with analysis light 142, in this case, for example, through the carrier element 112. The analysis light 142 can be optically filtered by at least one optional filter element 144.

The analyte detector 136 also can include an analyte photodetector 146 for absorbing detection light 148, for example, scattered analysis light. In this way, a reflectance value and/or a color change of the test chemical 119 can be observed. The detection light 148 optionally can be filtered by at least one filter element 150. It may be pointed out that numerous other possibilities of analyte detection and/or of the arrangement of the analyte detector 136 are also possible, for example, alternatively or additionally to a measurement of a reflectance value, the recording of a fluorescence. Accordingly, the analyte detector 136 would have to be modified. The analyte light source 140 and/or the analyte photodetector 146 can be designed, for example, as semiconductor construction elements, for example as a light-emitting diode or photodiode. Other embodiments are also possible.

The quality detector 136 also can include one or more units, where according to FIG. 1, two units are provided, which have a first luminescence in a first wavelength interval and a second luminescence in a second wavelength interval. Thus, the quality detector 138 includes two excitation light sources 152, 154, which optionally can be provided with filter elements 156, 158. These produce excitation light 160, 162. It may be pointed out that excitation light 160, 162 of different wavelengths could be generated by one and the same excitation light source 152, 154, such that these excitation light sources 152, 154 could also be combined, for example, where, for example, different filter elements 156, 158 could be used for producing excitation light 160, 162 of different wavelengths.

By means of the excitation light 160, 162, the test chemical 119 is irradiated, for example in turn through the transparent carrier element 112. This irradiation can take place simultaneously or else with a time delay. In the quality measurement, luminescence light 164, 166 is formed, which, optionally after filtering by optional filter elements 168, 170, is recorded by quality photodetectors 172, 174. The elements 152, 156, 168 and 172 thus form a first unit of the quality detector 138, for recording a first luminescence light, and the elements 154, 158, 170, 174, an optional second unit for recording a second luminescence light.

The ray paths shown in FIG. 1 are only shown schematically and can also be arranged in other ways. For example, for each ray incident on the test element 110, an angle of incidence a to an optical axis 175 perpendicular to the test element 110 and/or the carrier element 112 can be defined, and for each ray emerging from the test element 110 or parts thereof, scattered and/or emitted and/or reflected rays, an angle of emergence β. In FIG. 1, this is shown in the example of the analysis light 142 and of the detection light 148. Typically, the ray paths are chosen in such a way that for each incident ray and each associated ray emerging from the test element 110, for example, the rays 142 and 148, the angle of incidence α and the angle of emergence β are chosen differently. Thus, the relationship α>β can apply, as shown in FIG. 1, or conversely. In this way, a diffuse reflection and/or reflectance can be recorded. In fluorescence measurements too, excitation light customarily is irradiated at an angle, which is different to that angle at which an associated fluorescence and/or generally emission is recorded.

The analytical apparatus 130 in FIG. 1 also includes a control 176, which can also function as an evaluation device 178 and which, for example, can be connected to the analyte detector 136 and/or the quality detector 138 to control detectors 136, 138 and/or to evaluate signals from detectors 136, 138. The control 176 can include at least one data processing device. In addition, the control 176 can have one or more data stores 180 such as, for example, one or more databases. Furthermore, the control 176 can be equipped by means of one or more interfaces 182 to exchange information, data and/or orders with one or more further apparatuses. Moreover, the control 176 can interact with at least one user interface such as, for example, at least one display element 184 for the presentation of information and/or with one or more operating elements 186 for the input of orders and/or information by a user.

The analytical apparatus 130 shown in FIG. 7 can be arranged analogously to the exemplary embodiment shown in FIG. 1; however, instead of an individual test strip as a test element 110 a test tape is used, which can be part of a tape cassette 188. Tape cassette 188 can include a good reel 190 and a poor reel 192 and can be included interchangeably in the analytical apparatus 130. The test element 110 shown can include a carrier element 112 in the form of a carrier tape, which can be spooled stepwise from the good reel 190 to the poor reel 192 and which can comprise several test fields 116 analogously to the construction shown in FIG. 8, with the test chemical 119 and optionally the separating layer 122.

In turn, the analytical apparatus 130 in FIG. 7 includes an analyte detector 136 and a quality detector 138, which are only schematically indicated. For one possible construction of detectors 136, 138, reference can be made to the description of FIG. 1. FIG. 7, however, shows that detectors 136, 138 also can be arranged spatially offset from each other. Thus, a quality measurement position 194 and an analyte measurement position 196 are optionally provided, which are arranged spatially offset in a tape running direction 198 in such a way that the quality measurement position 194 is upstream of the analyte measurement position 196. In this way, the quality measurement can be carried out in such a way that a measurement of the intrinsic luminescence of the test chemical 119 is possible before placing of the sample 126.

In either exemplary embodiment, the analyte detector is at least one optical analyte detector. As used herein, "optical analyte detector" means a device that can carry out at least one analyte detection using one or more optical measuring methods. For example, the optical analyte detector can include at least one photodetector or at least one photosensitive semiconductor construction element such as a photodiode and/or a CCD camera. Optionally, the at least one optical analyte detector can include at least a light source to irradiate the test chemical with at least one analysis light, which can be at least excitation light and/or at least one light, which correspond to the reflection or reflectance properties of the test chemical and is reflected by the test chemical and/or influenced in another way by the test chemical. Alternatively, the at least one light source can emit at least one excitation light, which can excite the test chemical to at least a luminescence, in particular a fluorescence. The analytical apparatus can generally be configured to carry out in the analyte measurement by means of the optical analyte detector an optical recording of the property of the test chemical (i.e., a color measurement, a reflectance measurement and/or a fluorescence measurement).

The at least one optional light source can emit one or more wavelengths. The light emitted by the at least one light source is an analysis light, whereas the light recorded by the analyte detector is a detection light. The detection light can include analysis light after a diffuse scattering on the test element or parts thereof. Alternatively or additionally, the detection light can be a reflected analysis light or can be light emitted by the test chemical, where the light emission of this emitted light is excited by the analysis light. Thus, the analyte detector can record a diffuse reflection (i.e. a reflectance) on at least one layer of the test element.

In some instances, the quality detector can be supplied as a manual apparatus with a volume of not more than about 100 $cm^3$ or not more than 50 $cm^3$, so that it can be designed as a pocket apparatus to check the quality of test elements. The quality detector can include its own evaluation device and can have at least one display device, which is equipped to communicate to a user at least one result of the quality measurement. This display device can be of optical, acoustic, or haptic nature, so that appropriately information can be transmitted to the user about the result of the quality measurement. Thus, in the case of individual test strips equipped for reading according to a color scale, without use of an analyte detector, before use of the test strips a quality measurement of the type described can be carried out. In this manner, a use of degraded test elements for an analyte detection can be prevented or at least avoided. Such a quality detector is thus proposed as an independent subject in a further aspect of the present disclosure.

Methods

Methods also are provided that incorporate the inventive concept. Briefly, the analyte measurement step can be performed electrochemically and/or optically as is presently known in the art, using the at least one test chemical. For example, a reaction of the analyte to be detected with the test chemical or a part thereof can lead to a change in an amount of a detectable fluorophore, where the amount of the fluorophore correlates with the concentration of the analyte.

For detecting a measured variable characteristic, the amount of the fluorophore can be recorded. Such detection methods also are employable in the context of the present disclosure. In particular, fluorescence spectroscopy methods can be employed here such as, for example, the method described in EP Patent Application Publication No. 1780288 or in Int'l Patent Application Publication No. WO 2009/015870.

Briefly, in the quality measurement step, intrinsic luminescence of the test chemical (i.e., enzyme) can be measured directly. Alternatively, a substance can be admixed, which, like the enzyme, degrades similarly to the enzyme under identical temperature stress and/or moisture stress, and this degradation could be detected separately.

For measuring degradation of enzymes, activity determinations can be used. In some instances, eluates of the test element of, for example, a test strip can be generated and an activity of the enzyme(s) contained therein can be determined by means of an addition of a coenzyme and an analyte. The quality measurement and the quality detector are configured so that the quality measurement can be carried out nondestructively, which can be realized in the proposed measurement of the intrinsic luminescence.

As analytes, any desired biological or chemical substances can be determined that can be detected by a redox reaction (e.g., substances in which substrates of a coenzyme-dependent enzyme are concerned or coenzyme-dependent enzymes themselves). Examples of analytes include, but are not limited to, glucose, lactic acid, malic acid, glycerol, alcohol, cholesterol, triglycerides, ascorbic acid, cysteine, glutathione, peptides, urea, ammonium, salicylate, pyruvate, 5'-nucleotidase, creatine kinase (CK), lactate dehydrogenase (LDH), carbon dioxide, etc. In some instances, the analyte is glucose, which is detected with the aid of glucose dehydrogenase (GlucDH).

Figure 2:
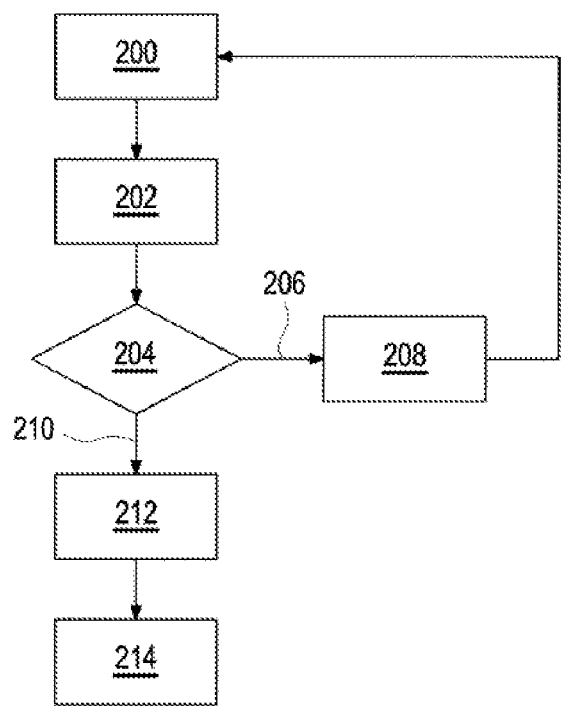
FIG. 2 shows an exemplary method.

FIG. 2 shows an exemplary embodiment of a method that can be carried out by means of the analytical apparatuses 130 according to the exemplary embodiments in FIGS. 1 and 7. In some instances, the control 176 can be equipped programmatically for this purpose to realize the method.

Thus, such a method can include a first step, which is designated in FIG. 2 as the start (reference number 200) and which can take place by means of an input of a test strip and/or by an opening of the analytical apparatus 130 and/or by an actuation of a start button. The start 200 also can include providing a new test element 110.

Subsequently, in step 202, a quality measurement can be performed, in which an intrinsic luminescence of the test chemical 119 is recorded before placing of the sample 126.

Subsequently, and in optional method step 204, an interrogation of the quality of the test element 110 determined in step 202 can occur. In this interrogation 204, the quality can be compared with one or more conditions by comparing the quality with one or more threshold values. Optionally a lack of quality can be determined (branch 206 in FIG. 2), which can indicate a degraded test element 110, a warning 208 can be generated and/or a termination can take place. Here, a user can be prompted to input a new test element 110 and/or a new start 200 of the method shown in FIG. 2 can take place.

If, on the other hand, it is found in step 204 that the quality is adequate for the continuation of the method (branch 2010 in FIG. 2), an analyte measurement 212 can be performed.

In the analyte measurement 212, a user, by means of the display element 184, can be prompted to add a sample 126 to the test element 110. Subsequently, and after an adequate reaction time for the detection reaction, an analyte measurement can be performed using the analyte detector 136 to measure reflectance, as is known in principle from the art. Other types of analyte measurements, however, also are contemplated.

In method step 214, an evaluation occurs, which can include determining or calculating a concentration of the analyte in the sample 126. The evaluation 214 optionally can be carried out using the quality determined in the quality measurement 202. Thus, for example, the evaluation 214 can take place to the effect that the results of the analyte measurement 212 taking into consideration the quality of the test chemical 119, an activity of at least one optional enzyme contained in the test chemical 119, are corrected. Examples of such a correction are illustrated below in greater detail. This correction can take place, for example, by means of correction factors and/or one or more correction functions and/or one or more correction values stored in the data store 180.

EXAMPLES

The inventive concept will be more fully understood upon consideration of the following non-limiting examples, which are offered for purposes of illustration, not limitation.

Example 1

Test Element Construction

In this example, layer structures of the test field are prepared as follows:
Detection Layer:
For producing a dispersion for the detection layer 118, firstly two partial solutions (partial solution 1 and 2) are prepared; these are then combined to give a partial batch. As used herein, "solution" is used in this connection independently of whether a true solution is actually present or only, for example, a dispersion. An enzyme solution was prepared, and the partial batch 1 and the enzyme solution were mixed, so that a coating material results. For this, the procedure was as follows:

Partial solution 1: 0.34 g of xanthan gum was pre-swollen in 35.5 g of 0.02 M glycerol 3-phosphate buffer of pH 6.5 for 24 h and mixed with 5.0 g of polyvinyl propionate dispersion.

Partial solution 2: 5.2 g of Transpafill was dispersed in 21.5 g of water for 10 min using an Ultraturrax.

Partial batch 1: Both partial solutions were combined and after adding 0.15 g of tetraethylammonium chloride, 0.17 g of N-octanoyl-N-methylglucamide, 0.06 g of N-methyl-N-octadecenyl taurate ("Geropon T 77") and 0.88 g of PVP (MW 25 000) were stirred moderately with a blade stirrer for 1 h. According to the series, the following partial solutions were then added:

0.10 g of bis(2-hydroxyethyl)-(4-hydroximinocyclohexa-2,5-dienylidine)-ammonium chloride in 1.5 g of water, and 0.65 g of 2,18-phosphormolybdic acid hexasodium salt in 1.5 g of water, whereupon the pH is adjusted to 6.7 with NaOH.

Enzyme solution: 5 mg of PQQ disodium salt and 0.28 g of GDH (mutant 31) and 0.16 g of a 1 M $CaCl_2$ solution were added to 25.6 g of 0.1 M glycerol 3-phosphate buffer of pH 6.5 and stirred for >3 h.

Partial batch 1 and enzyme solution were mixed, treated with a solution of 20 mg of $K_3[Fe(CN)_6]$ in 0.4 g of water and 1.0 g of 2-methyl-2-butanol and stirred for 30 min. A coating material for the production of the detection layer 118 resulted.

The coating material thus prepared was applied at an area weight of 90 $g/m^2$ to a carrier film 119 in the form of a polycarbonate film with a thickness of 125 μm and dried.

Transpafill® is a commercially obtainable sodium aluminum silicate powder of Evonik Industries AG. The precision-improving action of N-methyl-N-octadecenyl taurate ("Geropon T 77") is known and is described in EP Patent Application Publication No. 0995994.

Separating Layer:
Two partial solutions (partial solution 1 and partial solution 2) were also prepared for producing the separating layer 122, where were then combined. The procedure was as follows here:

Partial solution 1: A suspension of 1.37 g of Gantrez S 97 in 13.5 g of water was treated with 2.2 g of 16% NaOH and pre-swollen overnight. 0.40 g of tetraethylammonium chloride, 0.34 g of N-octanoyl-N-methylglucamide, 0.06 g of N-methyl-N-octadecenyl taurate ("Geropon T 77") and 1.87 g of PVP (MW 25 000) were added, and the mixture stirred for 1 h.

Partial solution 2: 14.3 g of titanium dioxide E 1171 from Kronos and 1.95 g of precipitated silica FK 320 from Degussa were dispersed in 36.4 g of water for 10 min using an Ultraturrax.

After combining the partial solutions, 5.7 g of polyvinyl propionate dispersion, 0.15 g of bis(2-hydroxyethyl)-(4-hydroximinocyclohexa-2,5-dienylidine)ammonium chloride in 4.2 g of water, 1.85 g of 2,18-phosphormolybdic acid hexasodium salt in 4.2 g of water and 10 mg of $K_3[Fe(CN)_6]$ in 0.4 g of water were added, and the mixture was adjusted to pH 6.8 using NaOH. After adding 1.0 g of 2-methyl-2-butanol, it was stirred for a further 1 h.

The name Gantrez® is a product name of ISP International Speciality Products, Cologne, Germany. Chemically, it is a copolymer of maleic acid and methyl vinyl ether.

The coating material thus prepared by combination of the partial solutions 1 and 2 was then applied with an area weight of 45 g/m² to the carrier film 119 of polycarbonate first coated as described above, that is to the detection layer 118, and dried.

Example 2

Analyte Measurements with an Test Chemistry Quality Measurement

In FIGS. 3 to 6C, different measurement examples are shown, which were obtained from enzymatic test chemicals. Thus, as explained above, in the course of general investigations on enzymatic detections, an initially surprising property of such test chemicals was found using at least one enzyme. This surprising property being that a degradation is associated with a change in an intrinsic luminescence, in particular an intrinsic fluorescence, of the test chemical that can be measured before wetting the test element with a fluidic sample. On micrographs of a fluorescence of CNAD test strips, initially qualitatively greatly different autofluorescences were observed after storage of these test strips at different temperatures (e.g., from 4° C. and 20° C.). After storage at 20° C., test strips showed markedly increased autofluorescence when compared to test strips stored at 4° C.

From these observations, subsequent investigations on the activity loss of the test chemical were carried out. Here, test elements were subjected to a special loading ("stress") by storing the test elements, in this case test strips, for several days at an elevated temperature (e.g., about 60° C.) and under increased atmospheric humidity (e.g., about 75% rH).

Figure 3:
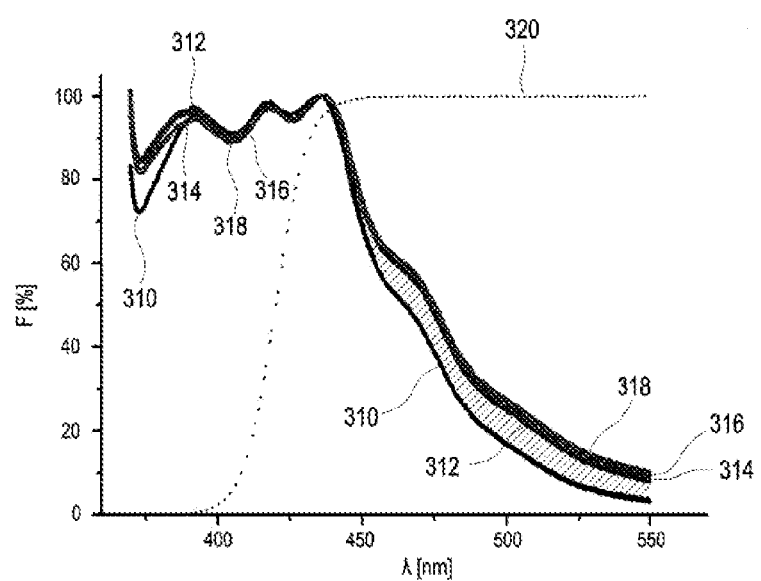
FIG. 3 shows intrinsic fluorescence of a test element after different aging processes.
Figure 4:
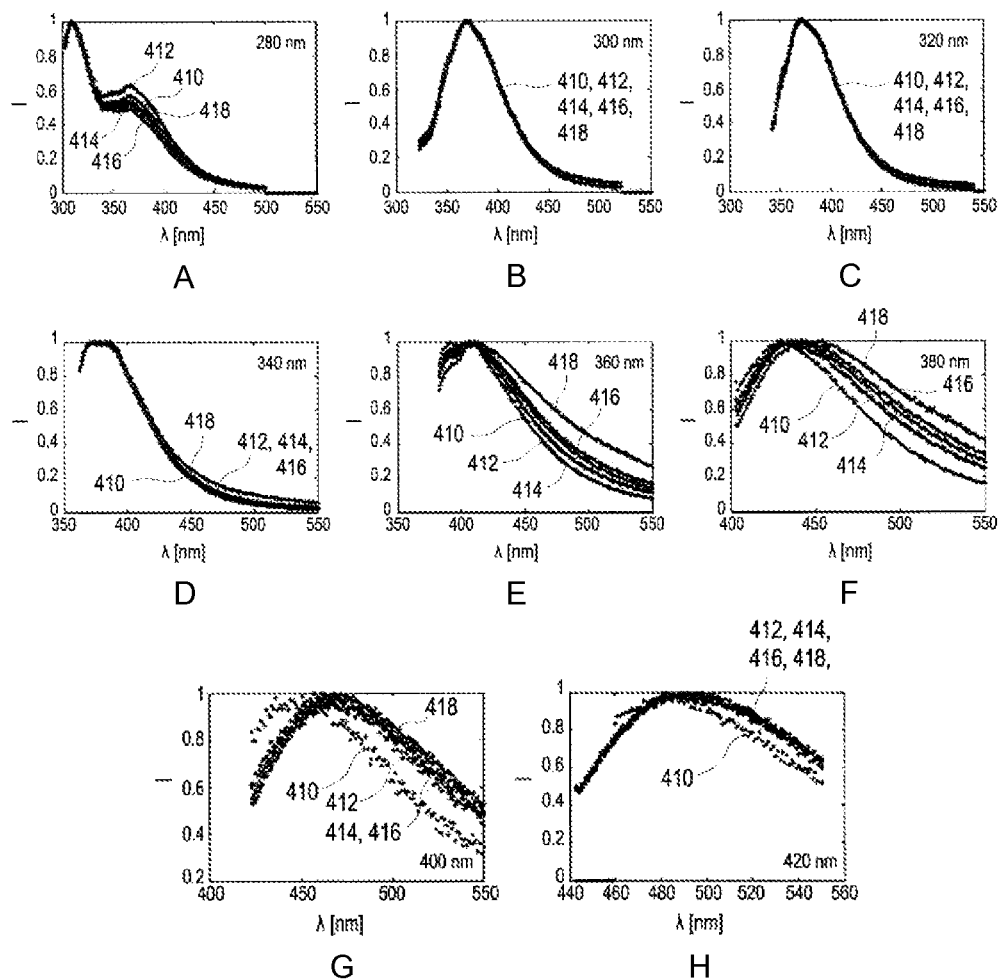
FIGS. 4A-H show intrinsic fluorescence of test elements after different storages at different excitation wavelengths.

FIG. 3 shows results of intrinsic fluorescence measurements of test elements treated in this manner. A relative fluorescence (standardized to a maximum value of 100%) is plotted as a function of the wavelength. Here, curve 310 indicates an intrinsic fluorescence of a test element before storage, immediately after preparation; curve 312 indicates an intrinsic fluorescence on the first day after the start of storage; curve 314 indicates an intrinsic fluorescence on the second day after the start of storage; curve 316 indicates an intrinsic fluorescence on the third day after the start of storage; and curve 318 indicates an intrinsic fluorescence on the fourth day after the start of storage.

The spectra 310 to 320 are in each case standardized to a peak at 440 nm. The excitation of the intrinsic luminescence in the measurements was carried out at an excitation wavelength of 360 nm. The increase in the autofluorescence of the test strips at wavelengths greater than 440 nm can be clearly recognized. Symbolically, a transmission curve of a filter characteristic 320 was plotted in FIG. 3, which could be used for one of the filter elements 168, 170 in the arrangement of the quality detector 138 according to FIG. 1 to absorb the increased autofluorescence at wavelengths above 440 nm. For example, a cut-off filter could be used for this, which is commercially available.

In FIG. 3, the measurements were carried out, differing from the construction of the test elements described above, using a carrier element in the form of a polyethylene terephthalate (PET) film (Melinex®). Accordingly, the fluorescence signal is still possibly influenced by scattered light fluorescence of the Melinex® carrier film. Interestingly, these first measurements in FIG. 3 show that a substance in the test elements leads to a fluorescence increase under stress conditions. Nevertheless, the results shown also could be reproduced with a slightly modified formulation of the test chemical, and the effect of the Melinex® film could be reduced by improving fluorescence spectroscopy. At the same time, the increase in the autofluorescence of the test elements could be reproduced, which is shown in FIGS. 4A-H.

In FIGS. 4A-H, fluorescence spectra of test elements for various excitation wavelengths of 280 nm (FIG. 4A) to 420 nm (FIG. 4H) are in turn shown. In each case, the fluorescence intensity (I), standardized to the respective peak within the recorded spectrum, is plotted again as a function of the wavelength (λ), indicated in nanometers (nm). The excitation wavelength is indicated in the figures. The measurements show that at an excitation wavelength of 360 nm to 400 nm with a fluorescence of >420 nm, the clearest differences result after different storage periods. In particular, in this area, and as already apparent from FIG. 3, the intrinsic fluorescence clearly increases with the storage period. This intrinsic fluorescence can thus be used as a criterion for a degradation detection. In particular, for simple quantification of a fluorescence change, a ratio of an integral intensity at wavelengths <420 nm and at wavelengths >420 nm can be formed. Thus, for example, generally a first intrinsic luminescence in a wavelength range <420 nm, such as a wavelength range of 380 nm to 420 nm, can be recorded, and a second intrinsic luminescence integrally in a second wavelength range >420 nm, such as >420 nm to <650 nm.

Figure 5:
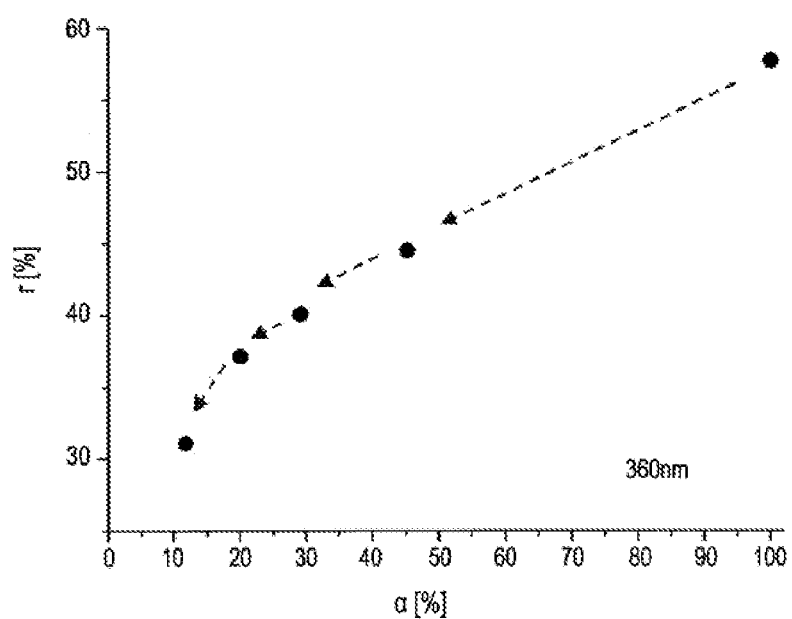
FIG. 5 shows a relationship between an enzyme activity and a ratio of an integral intensity of the intrinsic fluorescence at wavelengths smaller than about 420 nm to the integral intensity of the intrinsic fluorescence at wavelengths greater than about 420 nm at an excitation wavelength of about 360 nm.
Figure 6:
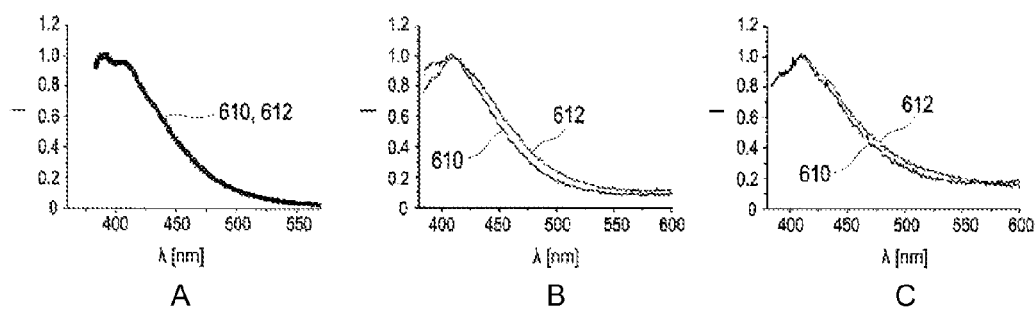
FIGS. 6A-C show fluorescence spectra of various completely or partially constructed test elements before and after aging.

As shown in FIG. 5, the intensity of the intrinsic luminescence (i.e., the said intensity ratio) represents a usable measure for quality of the test chemical. Thus, in FIG. 5, the intensity ratio (r) is indicated in percent, where this ratio (r) shows the ratio of the integral intensity at wavelengths <420 nm to the integral intensity at wavelengths >420 nm, indicated in percent. Fluorescence measurements are shown at an excitation wavelength of 360 nm.

On the horizontal axis, and as a comparison to this, the activity of the test chemical is indicated, which according to the above description was determined in an eluate of the test element according to the abovementioned measurement method. Here, an eluate of the test chemical was generated, and the activity of the enzymes contained therein was determined by means of a coenzyme and of an analyte in a laboratory analytical method. A connection between the laboratory-analytically determined activity and the intrinsic fluorescence is clearly to be found, where a decrease in the activity correlates with an increase in the intrinsic fluorescence at wavelengths >420 nm.

In further experiments, it was investigated to what extent the increased intrinsic luminescence and in particular intrinsic fluorescence directly or indirectly correlates with the activity decrease. Although an indirect relationship would be an option here, it is generally not desirable, as in this case in a real product situation the stress-induced modification process possibly of two components in constant relationship, for example from raw material via processing up to storage, would have to be kept constant. At the same time, this relationship conceptually could, in the case of the stress of 60° C. and 75% relative humidity chosen here, just exist randomly, whereas in the case of closer consideration the enzyme would possibly react primarily to a temperature stress and the unknown substance primarily to a humidity stress.

To this extent, it was desirable to be able to detect a modification of the enzyme directly. From the literature cited herein, it could be presumed that in the case of an excitation in the range from 340 nm to 380 nm, no autofluorescence of the enzyme itself was to be expected. Additionally, similar stress tests, although not on the identical enzyme, in the literature suggested that a conceivable fluorescence change under stress, if at all, should then lead to a decrease and not to an increase in the autofluorescence after stress.

To identify the fluorescent substance, test elements were therefore prepared in the laboratory, that only contained the carrier element and the above-mentioned Gantrez® S-97 contained in the literature (a copolymer of maleic anhydride and methy-loinyl ether) as a thickener, as well as in each case only one of the other starting materials. The pure carrier element (Pokalon®) was measured as a base material.

As shown in FIGS. 6A-C, the intrinsic fluorescence is in each case plotted on the vertical axis at an excitation wavelength of 360 nm, standardized to the maximum indicated in the observed wavelength interval, and on the horizontal axis the detection wavelength (λ) in nanometers. Here, the curves 610 in each case show fluorescence before storage, and the curves 612 show fluorescence after five days, that is on the fourth day after storage, at a stress of 60° C. and 75% relative humidity.

In FIG. 6A, the fluorescence of the Pokalon® film, which was used as the carrier element, is shown. It can be seen that Pokalon® shows no fluorescence differences before and after the stress, as the curves 610 and 612 coincide.

In FIG. 6B, a measurement on a Pokalon® film containing Gantrez® as well as the enzyme glucose dehydrogenase, is shown. From this presentation, it results that in in the wavelength range >420 nm, the intrinsic fluorescence after stress (curve 612) in comparison to an original state is markedly increased.

In FIG. 6C, measurements on elements containing a Pokalon® film, Gantrez® and the coenzyme cNAD are shown. Here, too, in turn, a slight increase in the intrinsic luminescence in a wavelength range >420 nm was found after stress.

The experiments thus show that in fact the enzyme, as well as possibly the coenzyme itself, causes the increase in the intrinsic luminescence of the test chemical. These experiments gave rise to the concept of using this increased intrinsic luminescence after stress to be able to detect a degradation of the test chemical, in particular enzyme degradation, in the test element directly using the properties of the test chemical. This increase in the intrinsic luminescence, especially the intrinsic fluorescence, is found in the case of test elements such as test strips before wetting with the sample (i.e., already before use by a user).

A system for detecting this intrinsic luminescence requires, as shown by way of example with the aid of FIGS. 1 and 7, usually only one photodetector which, by suitable choice of the filters, does not react to the excitation light, but all the more to the luminescence light formed in the excitation and in particular fluorescence light. For example, a photodiode with a suitable filter could detect the increased intrinsic luminescence, in particular intrinsic fluorescence. As already mentioned above, in principle also a number of quality photodetectors 172, 174 can be used, of which one detects fluorescence light from 380 nm to 420 nm and the other photodiode detects fluorescence light between 420 nm and 650 nm. From the measurement signals of these photodiodes or generally photodetectors, a difference could then be formed or, alternatively or additionally, these signals could be related to one another to obtain a measure value for the fluorescence activity and/or a quality of the test chemical. To be able to conclude from the measure value an activity of the test chemical (e.g., an enzyme activity), a correction curve such as a calibration curve could be used analogously to the curve shown in FIG. 5. It also is conceivable to form a difference of the two signals and then relate this difference to the mean value of the two signals. Many other combinations are conceivable such as, for example, referencing to the excitation light (e.g., a blank value reflectance or similar referencings).

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

LISTING OF REFERENCE NUMBERS

| | |
|---|---|
| 110 | test element |
| 112 | carrier element |
| 113 | irradiated light |
| 114 | detectable light |
| 116 | test field |
| 118 | detecting layer |
| 119 | test chemical |
| 120 | detection side |
| 122 | separating layer |
| 124 | test field surface |
| 126 | sample |
| 128 | application side |
| 130 | analytical apparatus |
| 132 | insertion slot |
| 134 | application position |
| 136 | analyte detector |
| 138 | quality detector |
| 140 | analyte light source |
| 142 | analysis light |
| 144 | filter element |
| 146 | analyte photodetector |
| 148 | detection light |
| 150 | filter element |
| 152 | excitation light source |
| 154 | excitation light source |
| 156 | filter element |
| 158 | filter element |
| 160 | excitation light |
| 162 | excitation light |
| 164 | luminescence light |
| 166 | luminescence light |
| 168 | filter elements |
| 170 | filter elements |
| 172 | quality photodetector |
| 174 | quality photodetector |

-continued

| 175 | optical axis |
| --- | --- |
| 176 | control |
| 178 | evaluation device |
| 180 | data store |
| 182 | interface |
| 184 | display element |
| 186 | operating element |
| 188 | tape cassette |
| 190 | good reel |
| 192 | poor reel |
| 194 | quality measurement position |
| 196 | analyte measurement position |
| 198 | tape running direction |
| 200 | start |
| 202 | quality measurement |
| 204 | interrogation quality |
| 206 | lack of quality |
| 208 | warning, termination |
| 210 | adequate quality |
| 212 | analyte measurement |
| 214 | evaluation |
| 310 | before storage |
| 312 | 1st day |
| 314 | 2nd day |
| 316 | 3rd day |
| 318 | 4th day |
| 320 | filter characteristic |
| 410 | before storage |
| 412 | 1st day |
| 414 | 2nd day |
| 416 | 3rd day |
| 418 | 4th day |
| 610 | before storage |
| 612 | 4th day |

The invention claimed is:

1. A method of measuring an analyte in a fluid sample, the method comprising the steps of:
measuring intrinsic luminescence of at least one test chemical of a test element to obtain at least one quality measurement, wherein the test element has at least one test field, the test field being an area in which at least one cohesive layer of the at least one test chemical is applied to a carrier element or is incorporated into the carrier element, wherein from at least one measured intrinsic luminescence a quality of the test chemical is related to degrading or aging of the at least one test chemical, and wherein the measuring of intrinsic luminescence of at least one test chemical is performed before a fluid sample is applied to the at least one test field of the test element; and
measuring at least one analyte in an applied fluid sample to obtain an analyte measurement result, wherein at least one electrical property or at least one optical property of the at least one test chemical changeable by presence of the analyte is recorded.

2. The method of claim 1, wherein the at least one intrinsic luminescence is recorded at a wavelength range from about 380 nm to about 420 nm.

3. The method of claim 2, wherein a second intrinsic luminescence is recorded at a wavelength range from about 420 nm to about 650 nm.

4. The method of claim 3, wherein the measuring intrinsic luminescence step comprises calculating a quality index from the at least one intrinsic luminescence and the second intrinsic luminescence or calculating a linear combination of intrinsic luminescences.

5. The method of claim 1, wherein the measuring intrinsic luminescence step comprises comparing the at least one measured intrinsic luminescence to at least one predetermined threshold and discarding the analyte measurement result if the at least one recorded intrinsic luminescence is above the at least one predetermined threshold.

6. The method of claim 1, wherein the measuring intrinsic luminescence step comprises correcting or compensating the analyte concentration based upon the at least one measured intrinsic luminescence.

7. The method of claim 1, wherein the at least one test chemical comprises an oxidase or a dehydrogenase.

8. The method of claim 7, wherein the dehydrogenase is selected from the group consisting of glucose 6-phosphate dehydrogenase (EC 1.1.1.49), NAD-dependent cholesterol dehydrogenase (EC 1.1.1.62), FAD-dependent glucose dehydrogenase (EC 1.1.99.10) and PQQ-dependent glucose dehydrogenase (EC 1.1.5.2).

9. The method of claim 1, wherein the at least one test chemical is L-amino acid dehydrogenase (E.C.1.4.1.5).

10. The method of claim 1, wherein the at least one test chemical is an aspartate aminotransferase or an alanine aminotransferase.

* * * * *